United States Patent
Hone et al.

(10) Patent No.: US 7,537,769 B2
(45) Date of Patent: May 26, 2009

(54) WEBBED IMMUNOGENS COMPRISING RECOMBINANT HUMAN IMMUNODEFICIENCY VIRUS (HIV) ENVELOPE GLYCOPROTEINS AND THE M9 SCORPION TOXIN

(75) Inventors: David Michael Hone, Rockville, MD (US); David Yetu Onyabe, Poolesville, MD (US)

(73) Assignee: Aeras Global TB Vaccine Foundation, Rockville, MD (US)

( * ) Notice: Subject to any disclaimer, the term of this patent is extended or adjusted under 35 U.S.C. 154(b) by 292 days.

(21) Appl. No.: 11/445,455

(22) Filed: Jun. 2, 2006

(65) Prior Publication Data
US 2007/0014814 A1 Jan. 18, 2007

(51) Int. Cl.
*A61K 39/385* (2006.01)
*A61K 39/21* (2006.01)
*A61K 38/00* (2006.01)

(52) U.S. Cl. .............................. 424/196.11; 424/208.1; 530/300

(58) Field of Classification Search ........................ None
See application file for complete search history.

(56) References Cited

OTHER PUBLICATIONS

Zhang, W., et al., 1999, Conformational changes of gp120 in epitopes near the CCR5 binding site are induced by CD4 and a CD4 miniprotein mimetic, Biochem. 38:9405-9416.*

Vita, C., et al., 1999, Rational engineering of a miniprotein that reproduces the core of the CD4 site interacting with HIV-1 envelope glycoprotein, Proc. Natl. Acad. Sci. USA, 96(23):13091-13096.*

Martin, L., et al., 2003, Rational design of a CD4 mimic that inhibits HIV-1 entry and exposes cryptic neutralization epitopes, Nat. Biotech. 21:71-76.*

Varadarajan, R., et al., 2005, Characterization of gp120 and its single-chain derivatives, gp120-CD4D12 and gp120-M9: implications for targeting the CD4i epitope in human immunodeficiency virus vaccine design, J. Virol. 79(3):1713-1723.*

* cited by examiner

*Primary Examiner*—Jeffrey S. Parkin
(74) *Attorney, Agent, or Firm*—Whitham Curtis Christofferson & Cook, P.C.

(57) ABSTRACT

HIV envelope immunogens that display multivalent epitopes are provided. The immunogens are aggregated, "webbed" HIV envelope immunogens in which native envelope structures are stabilized due to interactions with multimeric derivatives of M9 scorpion toxin.

14 Claims, 14 Drawing Sheets

Native HIV-1 gp41 (after Chan et al. 1997)

FP | N36 | S-S | C34 | nmAb epitope | TM | Cytoplasmic tail

Modified chimeric gp41

N36 | Ebola virus gp2 | C34 | nmAb epitope | TM

Figure 11

BamHI
gga tcc →go to kozak sequence

Kozak sequence
aat atg ggc →go to Tissue Plasminogen Activator leader sequence

Tissue Plasminogen Activator leader sequence (GenBank accession no. E02331)
a tggatgcaat gaagagaggg ctctgctgtg tgctgctgct gtgtggagca gtcttcgttt cgcccagcca ggaaatccat gcccgattca gaagaggagc caga (SEQ ID NO: 1) →go to linker

Linker
ggc ggc ggc →go to gp120 gp120 A/G recombinant (human codon optimized, Andre *et al*., J. Virol. 72: 1497; 1998)
agcgccagcgagaacctgtgggtgaccgtgtactacggcgtg
cccgtgtgggaggaggccgacaccccccctgttctgcgccagcgacgccaaggcctacagc
accgagaagcacaacgtgtgggccacccacgcctgcgtgcccaccgaccccaacccccag
gagatcctgctgaagaacgtgaccgagcccttcaacatgtggaagaacaacatggtggag
cagatgcacgaggacatcatcagcctgtgggacgagagcctgaagccctgcgtgaagctg
accccccctgtgcgtgaccctggactgcatcaacgccaacgtgtgcggcggcaacagcacc
ggcaacagcaccgaggccaacaccaccgcctgcagcagcgaggaggtgaagaactgcacc
ttcaacatcaccaccgagatccgcgaccgcgagaagaaggagtacgccctgttctacaag
ctggacgtggtgcagatcgacaagaacaacaccaaccgctaccgcctgctgaactgcaac
gtgagcaccatcaagcaggcctgccccaaggtgaccttcgaccccatccccatccactac
tgcgcacctgccggcttcgccatcctgaagtgcaacgagaagaacttcaccggcatcggc
aagtgcaagaacgtgagcaccgtgcagtgcacccacggcatcaagcccgtggtgagcacc
cagctgctgctgaacggcagcctggccgaggaggagatcgtgatccgcagcgagaacatc
accaacaacgccaagatcgtgatcgtgcagctgaacaagagcatcgagatcaactgcacc
aggcccagcaacaacacccgccgcagcatcagcttcggccctggccaggccttctacagc
accggcgaggtgatcggcgacatccgcaaggcccactgcaacgtgaacagcaagaactgg
accgagatgctgcaccgcgtgaagatccagctgaagaagttcttcagcaacaccaccaac
atcaccttcaaccagagcgccggtggcgacctggagatcaccacccacagcttcaactgt
aggggcgagttcttctactgcgacaccagcaacctgttcaacatcagcgacagcaacaac
agcaccagcgacagcaacgacaccatcaccatcccctgcaagatcaagcagatcgtgcgc
atgtggcagcgcgtgggccaggccatgtacgcccctcccatcgctggcaacatcatctgc
gtgagcaacatcaccggcctgctgctgacccgcgacggcggccacaacgtgaccaacgag
accgagatcttccgccctggcggaggcgacatgcgcgacaactggcgcagcgagctgtac
aagtacaagatcgtgaagatcaagcccctgggcatcgcccctacccgcgcacgccgcagg
gtggtggagcgcgagaagacc (SEQ ID NO: 2) → go to rigid linker Rigid linker ccc tcc tcc ccc (SEQ ID NO: 3) → go to N36 of gp41

Figure 12A

N36 of gp41 (Zeh et al., AIDS Res. Hum. Retroviruses 21: 17 (2005)

tcc ggc atc gtg cag cag cag tcc aac ctg ctg cgc gcc atc gag gcc cag cag cac ctg ctg aag ctg acc gtg tgg ggc atc aag cag ctg cag gcc cgc gtg ctg (SEQ ID NO: 4) →go to linker Linker
gag gcc→go to Ebola gp2

Ebola gp2 (residue 552-593, Sanchez *et al.*, Virus Res. 29: 215 (1993); Weissenhorn *et al.*, Proc. Natl. Acad Sci. USA 95: 6032 (1998))
gac ggc ctg atc tgc ggc ctg cgc cag ctg gcc aac gag acc acc cag gcc ctg cag ctg ttc ctg cgc gcc acc acc gag ctg cgc acc ttc tcc atc ctg aac cgc aag gcc atc gac ttc ctg (SEQ ID NO: 5)
→Go to linker Linker
ggc ggc ggc →Go to C34

C34 domain of gp41 (from CRF A/G )

tgg cgc gac tgg gac aag gag atc tcc aag tac acc cgc atc atc tac gac ctg atc gag gag tcc cag aac cag cag gag aag aac gag cag gac ctg ctg (SEQ ID NO: 6) →Go to COOH end of gp41

COOH end of gp41
gcc ctg gac aag tgg gcc tcc ctg tgg aac tgg ttc gac atc tcc aac tgg ctg tgg tac atc aag atc (SEQ ID NO: 7) →Go to transmembrane domain of gp41

Transmembrane domain of gp41 ttc atc atg atc gtg ggc ggc ctg atc ggc ctg cgc atc gtg ttc gcc gtg ctg tcc atc gtg (SEQ ID NO: 8) →go to linker Linker
ggc ggc ggc →go to polyHis tag PolyHis tag
cat cat cac cat cac cat tga (SEQ ID NO: 9) →go to *NotI*

*NotI*
gcg gcc gc

Figure 12B

*HindIII*
aag ctt→go to kozak

Kozak sequence aat atg ggc→go to Tissue Plasminogen Activator (tPA) signal peptide Human Tissue Plasminogen Activator signal peptide (GenBank accession no. E02331)
a tggatgcaat gaagagaggg ctctgctgtg tgctgctgct gtgtggagca gtcttcgttt cgcccagcca
ggaaatccat gcccgattca gaagaggagc caga (SEQ ID NO: 10) →go to linker Linker
ggc ggc ggc → go to M9

M9 (Vita *et al.*, Proc. Natl. Acad Sci. USA 96: 13091 (1999))
tgc aac ctg gcc cgc tgc cag ctg cgc tgc aag tcc ctg ggc ctg ctg ggc aag tgc gcc ggc tcc ttc
tgc gcc tgc gtg aag (SEQ ID NO: 11) → go to linker Linker ggc tcc tcc ccc tcc ccc tcc tcc ccc tcc ccc (SEQ ID NO: 12) → go to fibritin Bacteriophage T4 fibritin (Yang *et al.*, J Virol. 76: 4634 (2002)).

ggc tac atc ccc gag gcc ccc cgc gac ggc cag gcc tac gtg cgcaag gac ggc gag tgg gtg ctg ctg tcc acc ttc ctg (SEQ ID NO: 13) → go to linker Linker ggc ggc ggc →go to polyHis tag PolyHis tag cat cat cac cat cac cat tga (SEQ ID NO: 14) →go to *KpnI*

*KpnI*
ggtacc

Figure 13

WEBBED IMMUNOGENS COMPRISING RECOMBINANT HUMAN IMMUNODEFICIENCY VIRUS (HIV) ENVELOPE GLYCOPROTEINS AND THE M9 SCORPION TOXIN

This invention was made during work funded in part by grant number RO1-AI-055367 from the National Institutes of Health. The United States government may have certain rights in this invention.

BACKGROUND OF THE INVENTION

1. Field of Invention

The present invention provides HIV envelope immunogens that display multivalent epitopes. In particular, the immuogens are "webbed" HIV envelope immunogens in which native envelope structures are stabilized due to interactions with derivatives of M9 scorpion toxin.

2. Background of the Invention

Over 40 million people are infected worldwide with HIV-1, with the majority of cases in Africa (UNAIDS 2002). Although antiretroviral drugs can reduce viral replication and therefore slow immunopathogenesis, virtually all infected individuals progress to AIDS and ultimately death. Clearly, a vaccine is needed to control the spread of HIV.

It is likely that an effective HIV vaccine will consist of components that confer protection through CD8+ cytotoxic T lymphocytes (CTLs) and antibodies (Abs). CTLs can control replication of HIV and therefore slow pathogenesis, but do not prevent infection (see reviews in Letvin et al. Annu Rev. Immunol 20:73 (2002); McMichael and Hanke, Nature Rev. Immunol 2: 283(2002); Spearman 2003. Curr HIV Res 1:101 (2003)). Only Abs can completely prevent infection, resulting in so-called sterilizing immunity. Depending on the dosage, passive transfer of neutralizing monoclonal or polyclonal Abs against HIV-1 may confer sterile protection against challenge with pathogenic simian/human immunodeficiency chimeric virus in non-human primates (Mascola et al., J. Virol. 73: 4009 (1999); Mascola et al., Nat Med. 6:207 (2000); Parren et al., J. Virol. 75: 8340 (2001); Nishimura et al., Proc Natl Acad Sci USA. 100:15131 (2003)).

The exact mechanism by which antibodies confer protection in vivo or neutralize virus in vitro is unknown, but there is a positive correlation between protection and neutralization (Parren and Burton, Adv. Immunol 77:195(2001)). Neutralization probably occurs by the binding of Abs to a large number of sites on the virus, thus interfering with viral attachment to, and entry into host cells (Parren and Burton, Adv. Immunol 77:195(2001); Parren et al, J. Virol. 72: 3512 (1998); Burton, Nat. Rev. Immunol. 2:706 (2002)).

As alluded to above, the target of protective Abs to HIV is the 160 kDa envelope glycoprotein (Env). Env is synthesized as a precursor called gp160, which undergoes posttranslational modifications such as N-linked glycosylation and oligomerization in the endoplasmic reticulum (Earl et al., J. Virol. 65:2047 (1991)). Gp160 is cleaved by cellular proteases into gp120 and gp41 subunits in the Golgi apparatus (McCune et al, Cell 53: 55 (1988); Earl et al., J. Virol. 65: 2047(1991); Decroly et al, Febs Lett 405: 68 (1997); Hallenberger et al, J. Virol. 71: 1036 (1997)). Following cleavage, gp120 associates with gp41 through weak non-covalent interactions, and three gp120/gp41 dimers associate to form the mature Env trimer during transport to the cell surface (Kowalski et al, Science 237: 1351 (1987); Earl et al, J. Virol. 65:2047 (1991); Helseth et al., J. Virol 65: 2119 (1991)). The gp120 portion of the trimer is surface-exposed, whereas the gp41 portion of the trimer consists of a partially surface-exposed ectodomain, a transmembrane region, and a cytoplasmic tail that anchors the glycoprotein to the plasma membrane. Once Env trimers reach the surface of infected cells these molecules are incorporated into the budding virions through an interaction between the gp41 cytoplasmic domain and the capsid (Earl et al, Proc Natl Acad Sci USA. 87:648 (1990); Center et al, J Virol 76: 7863 (2002)).

During entry into a target cell, gp120 sequentially binds CD4 and chemokine receptors (such as CCR5 and CXCR4) on the target cell surface (Maddon et al, Cell 47: 333 (1986); Lifson et al., Nature. 323: 725 (1986); Dalgleish et al., Nature 312: 763 (1984); Klatzmann et al, Nature 312: 767 (1984); Deng et al., Nature 381: 661 (1996); Dragic et al, Nature 381: 667 (1996)). Receptor binding results in conformational changes that ultimately lead to fusion of viral and host cell membranes (a process believed to be mediated by the fusion peptide located at the N terminus of gp41) and, consequently, entry into the host cell.

Most Abs raised against envelope immunogens such as soluble monomeric gp120 or against the virus itself do not neutralize primary isolates of HIV-1 or protect the host from infection (Connor et al., J Virol 72: 1552 (1998); Mascola, J. Infect. Dis. 173: 340 (1996); Matthews, AIDS Res. Hum. Retroviruses 10: 631 (1994); Parren et al., AIDS 13 (Suppl. A):S137 (1999)). The molecular structure and antigenic properties of gp120 may in part explain the difficulty encountered in eliciting a neutralizing Ab response.

First, conserved epitopes that are located in parts of Env involved in cell entry, such as CD4- and coreceptor-binding sites are recessed within gp120 and poorly immunogenic (Kwong et al., Nature 393: 648 (1998); Wyatt et al., J Virol 69: 5723 (1995); Wyatt et al, Nature 393: 705 (1998)). Following CD4 binding, however, gp120 undergoes conformational changes that expose another class of conserved epitopes, namely CD4-induced (CD4i) epitopes, some of which are associated with the coreceptor-binding site in gp120 (Thali et al., J Virol 67: 3978 (1993); Wyatt et al., J Virol 69: 5723 (1995); Sullivan et al., J Virol 72: 4694 (1998)).

Second, the tertiary structure of the gp120 external surface has been divided into three functionally distinct domains: a neutralizing domain, a non-neutralizing domain, (Moore et al., J Virol 68: 469 (1994); Wyatt et al, Nature 393: 705 (1998)) and a silent domain (Wyatt et al, Nature 393: 705 (1998)). The non-neutralizing domain of gp120 is immunodominant in that it is highly immunogenic; however, Abs against this domain are non-neutralizing (Wyatt et al, Nature 393: 705 (1998)). Based on Ab-binding studies, it has been suggested that this domain is buried in the Env trimer but is exposed in monomeric gp120 and the uncleaved Env precursor, gp160 (Moore et al., J Virol 68: 469 (1994); Parren et al., Nat Med 3: 366 (1997); Wyatt et al, Nature 393: 705 (1998)).

Despite the difficulties discussed above, Ab-mediated protection against HIV is possible. Potent broadly neutralizing monoclonal antibodies (nmAbs) have been isolated from some HIV-positive patients that appear to be protected from progression to AIDS, or from experimental murine sources. The nmAbs include b12 (Burton et al., Science 266:1024 (1994)), X5 (Moulard et al., Proc Natl Acad Sci USA 99: 6913 (2002)), 2G12 (Trkola et al., J. Virol. 70: 1100 (1996)), m16 (Zhang et al., Antiviral Res 61: 161 (2004)), and m14 (Zhang et al., J Virol 78: 9233 (2004)) all of which recognize epitopes on gp120. A second subset of nmAbs, including 2F5 (Muster et al., J Virol 68: 4031 (1993)), Z13 (Zwick et al., J. Virol 75:10892 (2001)), and 4E10 (Stiegler et al, AIDS Res. Hum. Retroviruses 17: 1757 (2001)) binds to epitopes on gp41. Although the aforementioned nmAbs were raised against Env from clade B HIV-1 isolates, these nmAbs target conserved epitopes and each can neutralize isolates from other HIV-1clades in vitro, albeit with varying potencies (Zwick et al., J. Virol 75:10892 (2001); Stiegler et al., AIDS Res. Hum. Retroviruses 17: 1757 (2001); Trkola et al., J. Virol 69: 6609 (1995); Zhang et al., J Virol 78: 9233 (2004)). The challenge for HIV vaccine developers is to develop an immunogen that induces such Abs that display specificities similar to these broadly active nmAbs for a sustained period and therefore afford protection against an array of HIV-1 isolates.

Approaches to HIV Vaccine Design

During the early stages of HIV vaccine development, soluble monomeric gp120 was the most commonly used immunogen. However, it is now clear that gp120 elicits Abs that only neutralize HIV strains that express Env variants that were homologous to the gp120 or T cell line adapted (herein referred to as "TCLA") isolates, that is, HIV isolates that have been cultured extensively in T cells. This latter phenomenon has been attributed to the fact that TCLA strains are significantly more susceptible to neutralization than HIV-1 isolates that are maintained on primary human PBMC (Daar et al., Proc Natl Acad Sci USA. 87: 6574 (1990); Moore et al., J. Virol. 69: 101 (1995). Given that these so called primary HIV-1 isolates are more representative of the infectious form of HIV-1, the inability of gp120 vaccines to induce Abs that neutralize primary isolates is probably the reason such vaccines were ineffective in Vaxgen's phase 3 clinical trials of bivalent recombinant gp120 (Francis et al., AIDS Res. Hum. Retroviruses 14 Suppl 3: S325 (1998); Lee et al., Vaccine 20: 563 (2001)).

Given this inadequacy, there is interest in modifying gp120 so as to alter the immunodominance pattern and enhance the immunogenicity of conserved neutralizing epitopes in this molecule (Pantophlet and Burton, Trends Mol Med. 9: 468 (2003). One strategy entails the use of selective mutagenesis resulting in glycosylation of residues in the non-neutralizing domain to redirect the immune response away from this immunodominant region (Pantophlet et al., J Virol 77: 5889 (2003); Pantophlet et al., J Virol 77: 642 (2003). Although early reports demonstrate that this strategy indeed diminishes the immunogenicity of glycosylated regions (Pantophlet et al., supra (2003), the usefulness of this strategy is dependent on the development of technologies that enhance the immunogenicity of conserved neutralizing epitopes. Otherwise, the result of this approach will be to simply reduce the immunogenicity of gp120 for humoral immunity. A solution to this paradox has yet to emerge in the prior art.

Another approach to HIV immunogen development entails the construction of immunogens derived from Env that form stable trimers. The rationale for this approach is to generate immunogens that mimic the structure of native Env trimers displayed on virions during transmission. Indeed, scanning transmission electron microscopy of virus-associated Env confirmed the existence of the trimeric tertiary structure (Center et al, J Virol 76: 7863 (2002)). Furthermore, Ab-binding studies suggest that neutralization of HIV-1 correlates with binding to native trimeric Env but not to monomeric gp120 (Parren et al., J Virol 72: 3512 (1998); Fouts et al., J Virol 71: 2779 (1997); Sullivan et al., J Virol 69: 4413 (1995)). Finally, a serendipitous advantage of this approach is that the highly immunogenic non-neutralizing domain of gp120 becomes occluded in the trimer form, which may quench the immunodominance of this domain and redirect the immune response to the neutralizing domain (Wyatt et al, Nature 393: 705 (1998)).

To construct stable trimeric Env immunogens, amino acids that enable the formation of gp41 trimers and gp120-gp41 interaction, which are necessary for the production of stable trimers, must be stabilized. Gp41 trimer formation has been enhanced by creating genetic fusions wherein the GCN4 trimer motifs, derived from a yeast transcription factor, or a T4 bacteriophage fibritin trimer motif were introduced into the carboxyl end of the ectodomain of gp41 (Yang et al., J Virol 74: 5716 (2000); Yang et al., J Virol 74: 4746 (2000); Yang et al., J Virol 76: 4634 (2002)). Antisera raised in mice (Yang et al., J Virol 75: 1165 (2001)) or macaques (Srivastava et al., J Virol 77: 11244 (2003)) against such trimeric Env immunogens neutralize heterologous primary isolates; however, the serum dilutions required to achieve 50 percent inhibition of HIV infectivity were usually between 1:40 and 1:20. Therefore, although this approach has some merit, immunogenicity of neutralizing epitopes in such trimeric Env immunogens thus far generated was poor and is considered to be too low to afford long-lived protection in human populations.

Stabilization of the gp120-gp41 interaction can be accomplished using one of two strategies. The first approach entails mutagenesis of the proteolytic cleavage site between gp120 and gp41; however, without additional modification proteolytically uncleaved Env tends to assemble into dimers and tetramers (Earl et al., Proc. Natl. Acad Sci USA 87: 648 (1990); Earl et al., J Virol 68: 3015 (1994); Earl et al., J Virol 71: 2674 (1997)). As an alternative, intersubunit disulphide bonds were introduced to stabilize the interaction between gp120 and gp41 (Binley et al., J Virol 74: 627 (2000); Yang et al., J Virol 74: 4746 (2000)).

A third strategy to modify gp120 entails exposing conserved CD4i epitopes in gp120. During HIV-1 entry into host cells, gp120 binds CD4 (Maddon et al., Cell. 47: 333 (1986); Lifson et al., Nature. 323: 725 (1986)) and undergoes conformational changes that expose conserved epitopes that are involved in coreceptor binding (such as CCR5 or CXCR4 chemokine receptors; Sattentau and Moore J Exp Med 174: 407 (1991); Jones et al., 1998 J Biol Chem 273: 404 (1998)). Evidence for the existence of CD4i epitopes was generated by studies showing that CD4-binding to gp120 enhances affinity of certain HIV-specific mAbs, including 17b and 48d, to the gp120-CD4 complex (Thali et al., J Virol 67: 3978 (1993)). Binding of mAbs to CD4i epitopes inhibits binding of the gp120-CD4 complex to CCR5, suggesting that such antibodies bind to or occlude the conserved coreceptor binding site, which is exposed only after gp120 binds to CD4 (Wu et al., Nature. 384: 179 (1996)). Indeed, structural studies suggest that the binding of gp120 to CD4 results in movement of the V1/V2 loops, thereby exposing the otherwise shielded coreceptor binding site (Wyatt et al., J Virol 69: 5723 (1995); Sullivan et al., J. Virol 72: 4694 (1998)).

Given the importance of CD4i epitopes in HIV infectivity, one approach to inducing broadly nmAbs to HIV is to create gp120 immunogens that surface-expose and lock-in-place CD4i epitopes (Pal et al., Virology 194:833 (1993); DeVico et al., Virology 218: 258 (1996); Hone et al., J Hum Virol 5: 17 (2002); Fouts et al., FEMS Immuno Med Microbiol 37: 129 (2003)). Indeed, gp120 or gp140 chemically cross-linked to soluble human CD4 (shCD4), or genetic fusions of gp120 and the D1D2 domains of human CD4induce antibodies in mice, goats and macaques that neutralize primary HIV-1 isolates across clades and regardless of coreceptor usage (DeVico et al., Virology 218: 258 (1996); Fouts et al., Proc Natl Acad Sci USA 99: 11842 (2002); Onyabe et al, unpublished)). It is worth noting that in both the goat and macaque studies, the source of gp120 in the complex was a TCLA strain (HIV-$1_{IIIB}$), yet it elicited Ab that neutralized primary isolates.

Despite the encouraging observations above, concern over the use of human CD4 in a vaccine will hinder development of such immunogens beyond the laboratory. To circumvent the regulatory problems associated with the use of CD4, a CD4 mimetic, called M9 (Vita et al., Proc Natl Acad Sci USA 96: 13091 (1999), has the potential to be used in such immunogens. M9 is derived from scorpion toxin and competes with CD4 for binding to gp120 (Vita et al., Proc Natl Acad Sci USA 96: 13091 (1999); Zhang et al., Biochemistry. 38: 9405 (1999); Martin et al., Nat Biotech 21: 71 (2003)). More importantly, M9 and analog derivatives of this molecule induce conformational changes that expose CD4i epitopes (Vita et al., Proc Natl Acad Sci USA 96: 13091 (1999); Zhang et al., Biochemistry. 38: 9405 (1999); Martin et al., Nat Biotech 21: 71 (2003)), prevent cell-cell fusion of mammalian cells expressing HIV-1 envelope, and neutralize infectivity of HIV-1 strains in vitro regardless of coreceptor usage (Vita et al., Proc Natl Acad Sci USA 96: 13091 (1999); Martin et al., Nat Biotech 21: 71 (2003)). Unfortunately, a recent report indicated that gp120-M9 fusion protein failed to induce neutralizing antibodies to primary HIV isolates (Varadarajan et al. J. Virol. 79: 1713 (2005)).

It is clear from the foregoing discussion that the HIV Env immunogens currently available do not elicit high-titer broadly neutralizing antibodies to HIV. Therefore, there continues to be a need to develop HIV Env immunogens that induce antibodies that display broad specificity to native epitopes on HIV virions and/or possess broadly neutralizing activity against a wide array of primary HIV isolates.

SUMMARY OF THE INVENTION

The present invention describes a novel and unexpected finding that "webbed" HIV Env immunogens stabilize the trimeric structure of Env and display multivalent native Env and CD4i epitopes. Heretofore, there has been no documented report of such webbed HIV Env immunogens. That is, the present invention provides the first documentation of said immunogens.

The present invention provides webbed HIV envelope immunogens that display high-valency epitopes. Webbed HIV envelope immunogens are unique due to the capacity of the underlying antigen formulation strategy to stabilize native envelope structures and to produce aggregates of envelope oligomers bound either stoichiometrically or non-stoichiometrically to oligomerized ligands of the envelope. The webbed antigen is formed by non-covalent bonding between an Env protein and a derivative of scorpion M9 toxin. The webbed HIV envelope immunogens are useful for the generation and production of an HIV vaccine. Methods are provided to formulate webbed HIV envelope immunogens and for the use of webbed HIV envelope immunogens, for example, by direct administration as a subunit vaccine, incorporated into nucleic acid vaccines, formulated in adjuvants, or incorporated into vaccine vectors.

The invention thus provides a webbed HIV-1 envelope immunogen, comprising at least one recombinant HIV-1 envelope protein or truncated derivative thereof, and a multimer of a recombinant derivative of M9 domain of scorpion toxin. The at least one recombinant HIV-1 envelope protein or truncated derivative thereof and the multimer of a recombinant derivative of M9 domain of scorpion toxin are associated with one another. In preferred embodiments of the webbed HIV-1 envelope immunogen:

a) the recombinant derivative of M9 domain of scorpion toxin is fused to a peptide that promotes trimerization;

b) the at least one recombinant HIV-1 envelope protein or truncated derivative thereof is a trimer;

c) the at least one recombinant HIV-1 envelope protein or truncated derivative thereof is a recombinant HIV-1 envelope protein selected from the group consisting of subtype A, subtype B, subtype C, subtype D, subtype E, subtype J and clade G;

d) the at least one recombinant HIV-1 envelope protein or truncated derivative thereof is a truncated derivative selected from the group consisting of rgp160, rgp140, rgp120, rgp160$_3$ and rgp140$_3$;

e) an amino-terminal fusion domain and an immunodominant domain located between residues N36 and C34 of a gp41 portion of said webbed HIV-1 immunogen is deleted.

f) a disulfide loop of gp41 is replaced by a residue 552 to 593 heptad repeat domain from Zaire subtype Ebola virus gp2;

g) the webbed HIV-1 immunogen further comprises a rigid linker between gp120 and gp41;

h) the peptide that promotes trimerization is trimeric motif of bacteriophage T4 fibritin or GCN4;

i) the recombinant derivative of M9 domain of scorpion toxin comprises a reporter tag;

j) the reporter tag is selected from the group consisting of a His tag sequence from ETDuet-1;

k) either or both the recombinant HIV-1 envelope protein or truncated derivative thereof, and said multimer of a recombinant derivative of M9 domain of scorpion toxin comprise a leader sequence;

l) the leader sequence is from a source selected from the group consisting of human tissue plasminogen activator signal peptide, human interferon, human chromogranin, humans casein beta, tumor rejection antigen-1 gp96, and human zona pellucida glycoprotein 2 preprotein;

m) the at least one recombinant HIV-1 envelope protein or truncated derivative thereof and the multimer of a recombinant derivative of M9 domain of scorpion toxin are associated by hydrogen bonding; and n) the at least one recombinant HIV-1 envelope protein or truncated derivative thereof and the multimer of a recombinant derivative of M9 domain of scorpion toxin are associated by van der Waals forces.

The present invention also provides a composition for forming a webbed HIV-1 envelope immunogen. The composition comprises a first vector encoding at least one recombinant HIV-1 envelope protein or truncated derivative thereof; and a second vector encoding at least one recombinant derivative of M9 domain of scorpion toxin. In preferred embodiments of the invention:

a) the first and second vectors may be the same or different and are selected from the group consisting of plasmids, viral vectors, recombinant double strand RNA phage vectors, cloning vectors and expression vectors; and b) the first and second vectors are contained within a common pharmaceutically acceptable carrier.

The present invention also provides an HIV vaccine. The vaccine comprises a first vector encoding at least one recombinant HIV-1 envelope protein or truncated derivative thereof; and a second vector encoding at least one recombinant derivative of M9 domain of scorpion toxin. Preferred embodiments of the vaccine include:

a) the first and second vectors are contained within a common pharmaceutically acceptable carrier; and b) the first and second vectors are respectively contained within first and second pharmaceutically acceptable carriers, and wherein the first and second pharmaceutically acceptable carriers may be the same or different.

The present invention also provides a vector encoding a webbed HIV-1 envelope immunogen. The vector comprises at least one recombinant HIV-1 envelope protein or truncated derivative thereof, and at least one recombinant derivative of M9 domain of scorpion toxin. In preferred embodiments of the invention:

a) the vector is selected from the group consisting of plasmids, viral vectors, recombinant double strand RNA phage vectors, cloning vectors and expression vectors;
b) an at least one recombinant HIV-1 envelope protein or truncated derivative thereof, and an at least one recombinant derivative of M9 domain of scorpion toxin are encoded as separate molecules;
c) the at least one recombinant HIV-1 envelope protein or truncated derivative thereof, and the at least one recombinant derivative of M9 domain of scorpion toxin are encoded as a single molecule;
d) the vector is contained within and expressed by non-pathogenic or attenuated bacteria;
e) the vector is contained within and expressed by yeast;
f) the vector is contained within and expressed by a mammalian cell;
g) vector is pVAX1; the at least one recombinant HIV-1 envelope protein or truncated derivative thereof is rgp140, which further comprises a rigid linker between rgp120 and rgp41; a disulfide loop of rgp41 is replaced by a residue 552 to 593 heptad repeat domain from Zaire subtype Ebola virus gp2; and the at least one recombinant HIV-1 envelope protein or truncated derivative thereof further comprises a leader sequence from tissue plasminogen activator; and
h) the vector is pVAX1; the at least one recombinant derivative of M9 domain of scorpion toxin is fused to trimeric motif of bacteriophage T4 fibritin; the at least one recombinant derivative of M9 domain of scorpion toxin further comprises a His tag; and the at least one recombinant derivative of M9 domain of scorpion toxin further comprises a leader sequence from tissue plasminogen activator.

The invention further provides an antibody specific for a webbed HIV-1 envelope immunogen. The webbed HIV-1 envelope immunogen comprises at least one recombinant HIV-1 envelope protein or truncated derivative thereof, and a multimer of a recombinant derivative of M9 domain of scorpion toxin. In a preferred embodiment of the invention, the antibody is a monoclonal antibody.

BRIEF DESCRIPTION OF THE DRAWINGS

FIG. 8. Schematic representation of rgp $140_3$.
FIG. 9. Schematic representation of webbed rgp $160_3$; webbing is due to addition of M9::T4 fibritin.
FIG. 10. Schematic representation of webbed rgp $140_3$; webbing is due to addition of M9::T4 fibritin.
FIG. 11. Schematic representation of modifications of HIV-1 gp41.
FIG. 12 A and B. Flow chart/diagram showing the nucleotide sequence of components of HIV-1 rgp140$_3$. A, BamHI site through rigid linker; B, N36 of gp41 through NotI site.
FIG. 13. Flow chart/diagram showing the nucleotide sequence of components of chimeric M9::T4 fibritin.

DETAILED DESCRIPTION OF THE PREFERRED EMBODIMENTS OF THE INVENTION

Since Env is the only surface-exposed viral protein in the mature HIV-1 virion, it is considered to be the sole target of Abs that protect against HIV infection. An object of the present invention is to enhance the immunogenicity of conserved epitopes in Env by providing webbed Env immunogens that display multivalent conserved epitopes.

An epitope is defined herein as the specific site on an antigen to which a complementary antibody binds. A multivalent epitope is defined herein as an epitope that is present in multiple copies in a webbed immunogen (i.e. four or more copies). The initial association of an antibody with an epitope is mediated by relatively weak hydrogen bonds, electrostatic forces, and van der Waals forces. However, multivalent epitopes can stabilize antibody-antigen complexes, thereby improving the immunogenicity of such epitopes. Multivalent epitopes are also capable of inducing T cell-independent antibody responses (Mond et al., Annu Rev Immunol. :13:655 (1995)). An example of a naturally produced multivalent epitope is the H-serotype epitope, H-i, displayed by *Salmonella enteriditis* serotype *typhimurium* flagella (de Vries et al., Appl Environ Microbiol. 64:5033 (1998)).

To generate multivalent epitopes, recombinant HIV-1 Env (i.e. rgp160) or truncated recombinant derivatives of Env, including rgp140 (Binley et al., J. Virol. 74: 627 (2000); Yang et al., J. Virol. 74: 5716 (2000); Yang et al., J. Virol. 74: 4746 (2000)) and rgp120 (McKeating et al., J. Virol. 67: 4932 (1993); Robey et al., Proc. Natl. Acad. Sci. USA 83: 7023 (1986)) are assembled into aggregates, without denaturing the native tertiary structure of these macromolecules. Accordingly, the present invention provides novel webbed HIV-1 Env immunogens that are comprised of Env (or truncated derivatives of Env, such as rgp140 and rgp120) either covalently or non-covalently bound to a dimeric, trimeric, tetrameric or oligomeric derivative of M9.

By "derivative of M9" we mean a genetic fusion comprised of M9 and a motif that mediates the intermolecular association between two or more M9 molecules, thereby resulting in dimer, trimer, tetramer or oligomer formations of M9. In a preferred embodiment, M9 is genetically fused to the alpha-helical trimer motif of bacteriophage T4 fibritin; this product is referred to herein as M9$_3$.

By "Env" or "rgp160" we mean recombinant, uncleaved precursor gp160 comprised of gp120 and unmodified gp41 (i.e. the disulfide loop and cytoplasmic tail of gp41 are present). Rgp160 is illustrated in FIG. 12A, where the gp120 moiety, which contains the CD4 binding site, is depicted as attached to a gp41 moiety. The gp41 moiety comprises N36, a disulfide loop, C34, nmAbs epitope, a transmembrane domain, and a cytoplasmic tail.

Figure 1:
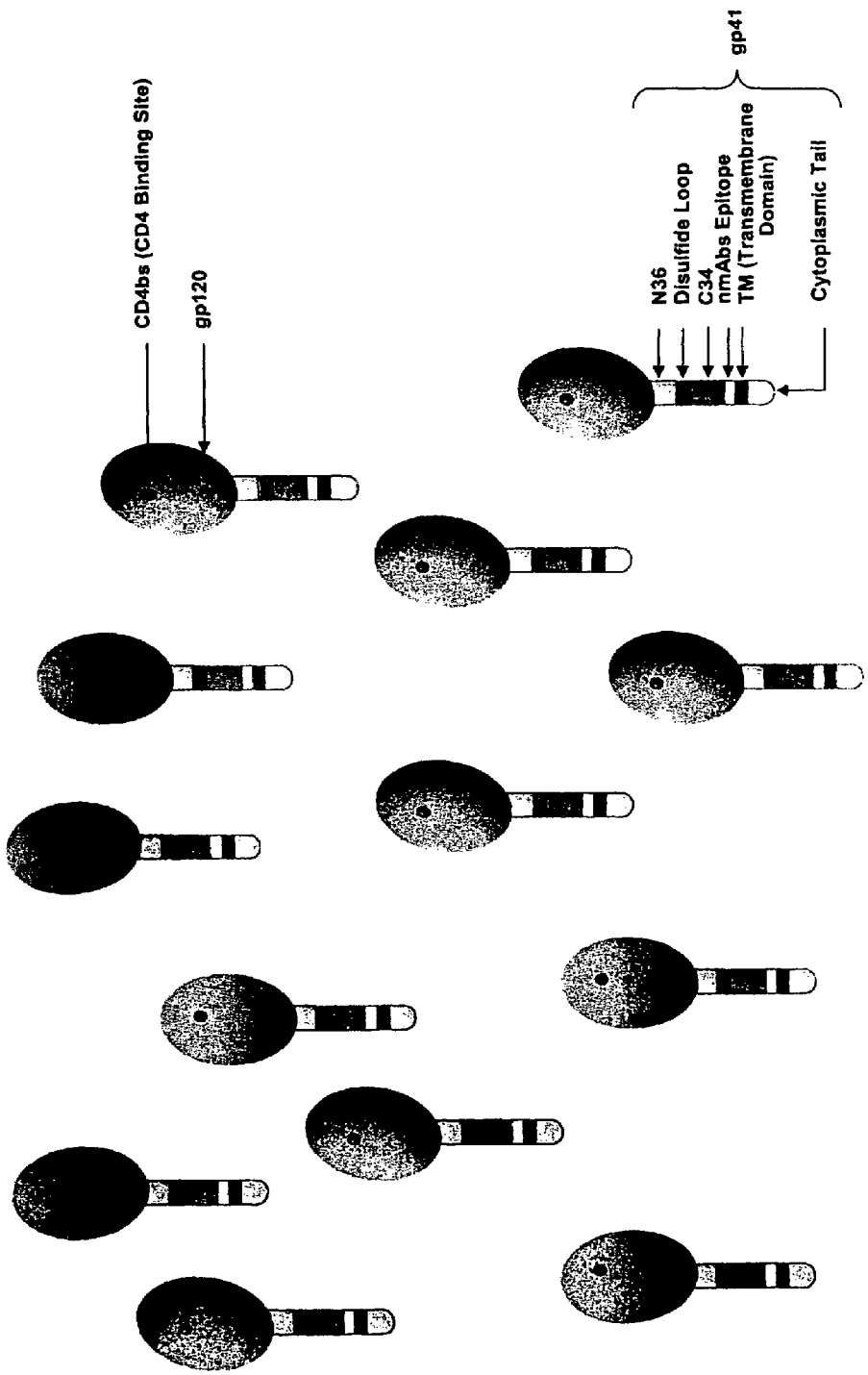
FIG. 1. Schematic representation of rgp160.
Figure 2:
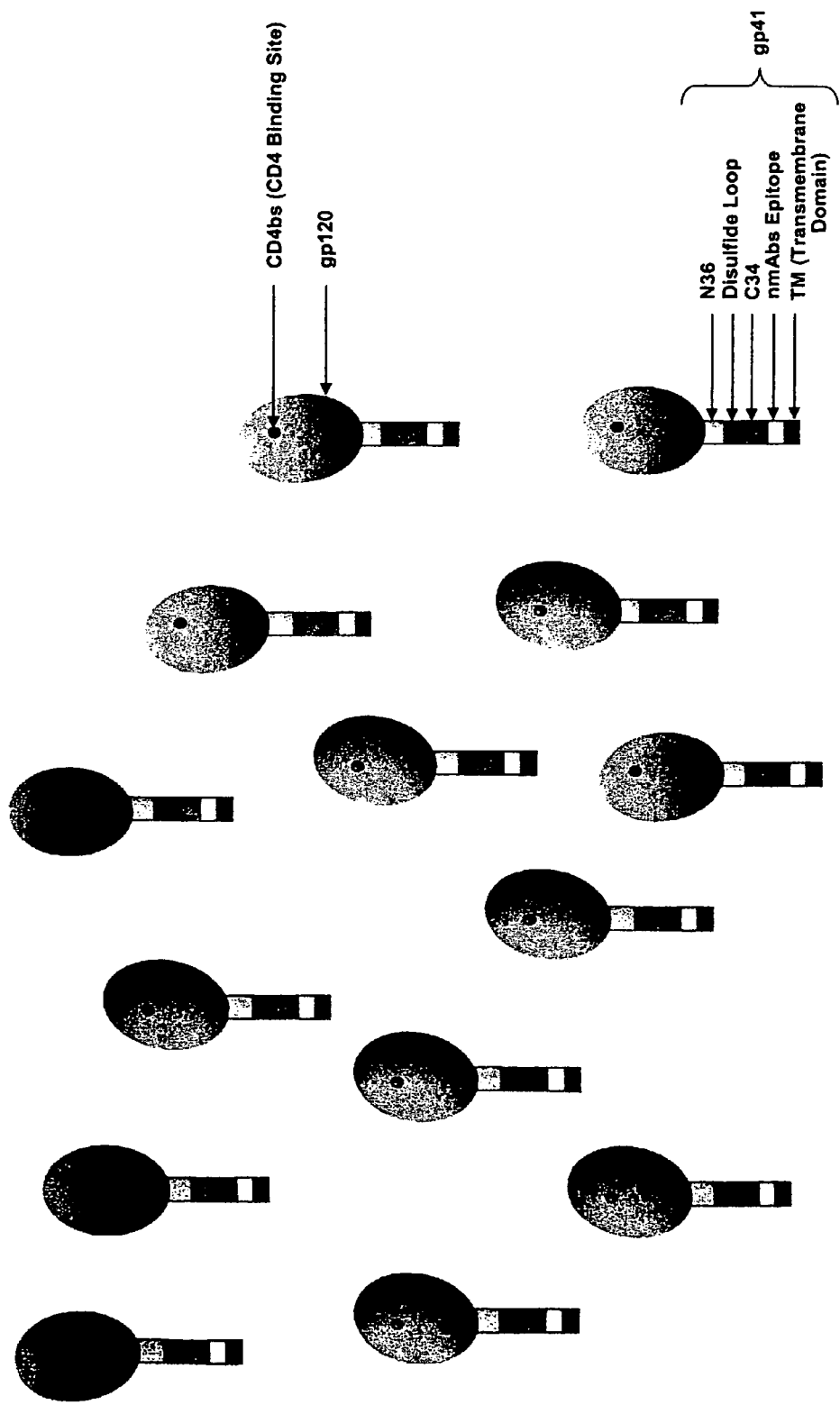
FIG. 2. Schematic representation of rgp 140.

By "rgp140" we mean a recombinant molecule comprising gp120 and a modified form of gp41 from which the cytoplasmic domain has been removed, but which retains N36, the disulfide loop, C34, nmAbs epitopes, and the transmembrane domain. Rgp 140 is depicted schematically in FIG. 2.

Figure 3:
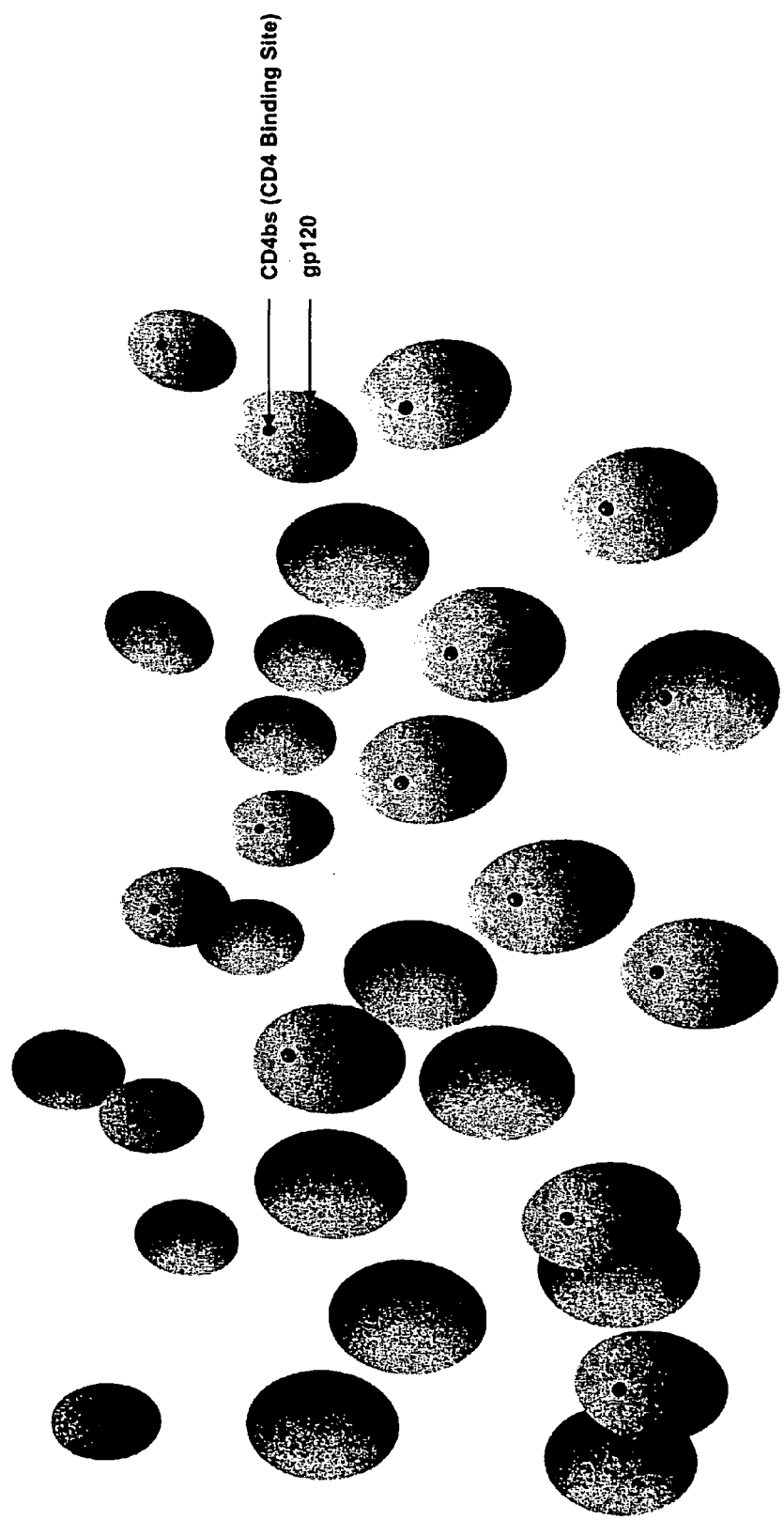
FIG. 3. Schematic representation of rgp 120.

By "rgp120" we mean a recombinant molecule containing the gp120 portion of gp160, without gp41. Rgp120 is depicted schematically in FIG. 3.

Figure 4:
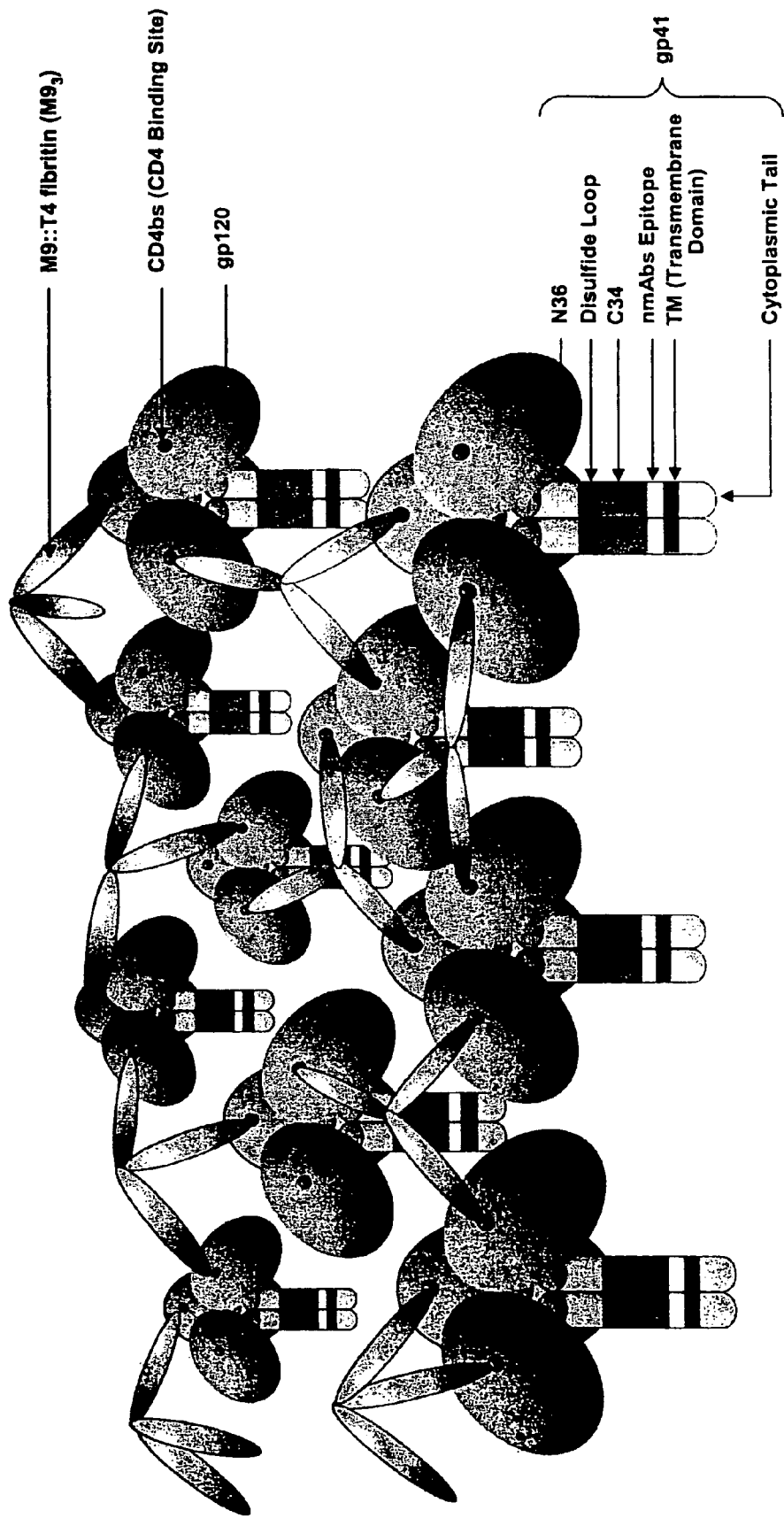
FIG. 4. Schematic representation of webbed rgp160; webbing is due to the addition of M9::T4 fibritin.
Figure 5:
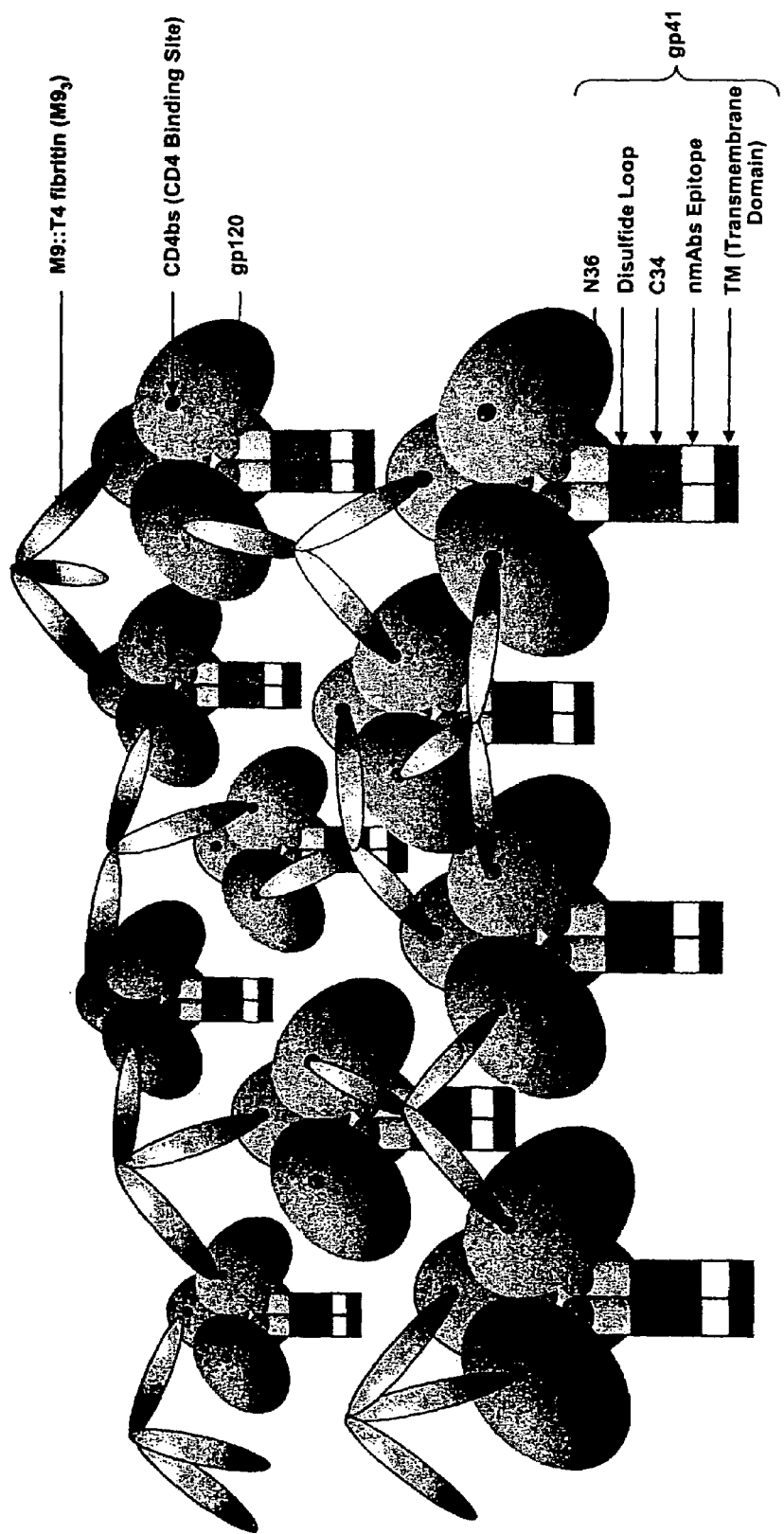
FIG. 5. Schematic representation of webbed rgp 140; webbing is due to addition of M9::T4 fibritin.
Figure 6:
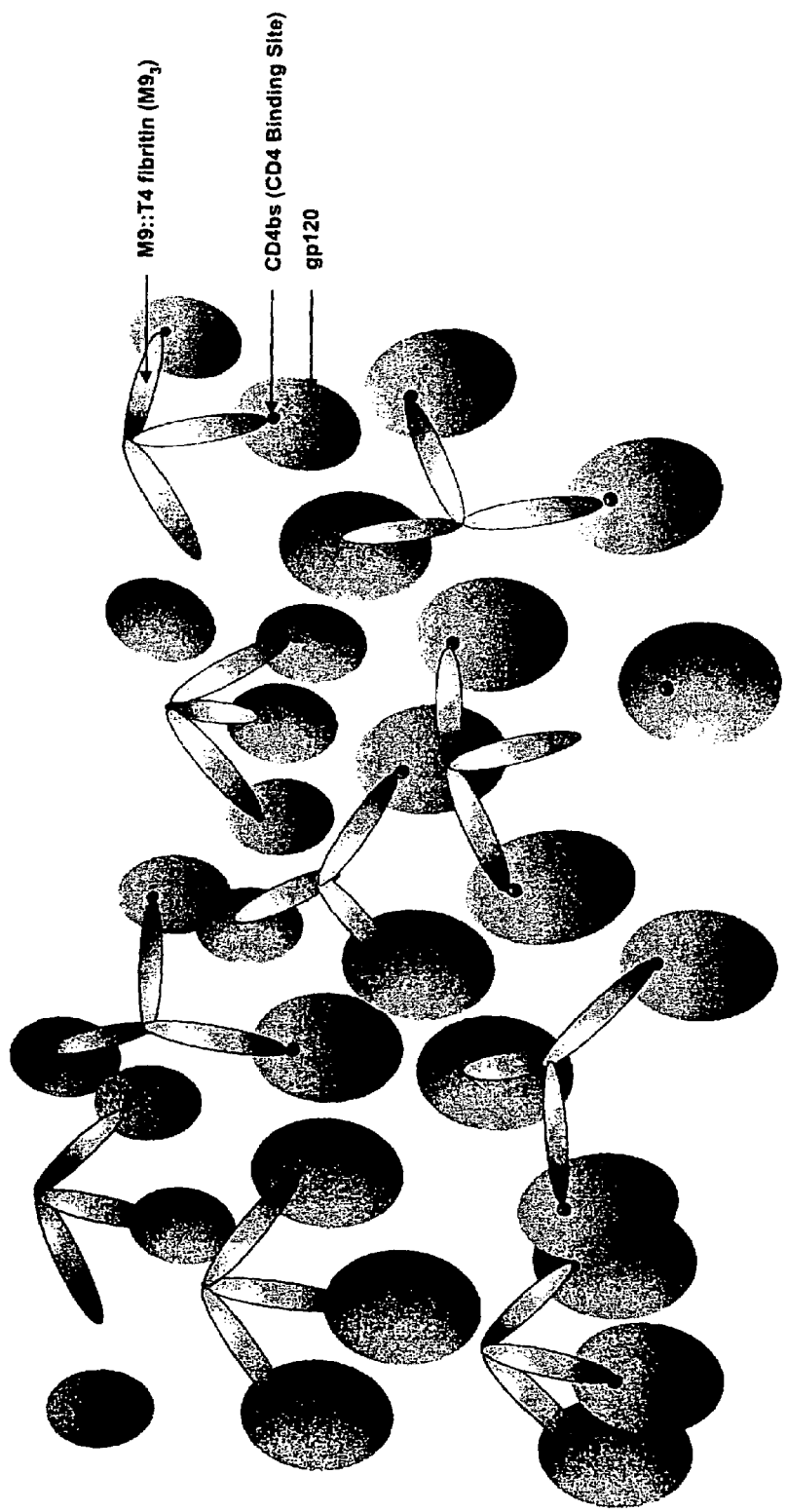
FIG. 6. Schematic representation of webbed rgp 120; webbing is due to addition of M9::T4 fibritin.

According to the present invention, the novel M9 derivatives are incorporated into various configurations with HIV Env immunogens (and derivatives thereof as described above). Such admixtures aggregate the immunogens in a manner analogous to the effect of adding an antibody to an antigen (Coligan et al., "Assays for antibody production," In: Current Protocols in Immunology, Vol. 1, pp. 2.1.1, John Wiley and sons, Inc (2003)). The mixtures thus form aggregates, herein referred to as "webbed" immunogens. The webbed immunogens display native Env epitopes multivalently, and stabilize the interaction between B cells and the webbed immunogen, resulting in surprising immunogenicity. Examples of such configurations are as follows:

1. Admixtures may be formed which contain rgp160 and an M9 derivative (i.e. dimer, trimer, tetramer or oligomer). An exemplary trimeric webbed antigenic immunogen of rgp160 and the M9 derivative M9::T4 fibritin ($M9_3$) is schematically depicted in FIG. 4. Note that the rgp41 moiety of the rgp160 molecule retains a cytoplasmic tail and a disulfide loop.
2. Similarly, admixtures may be formed which contain rgp140 and an M9 derivative (i.e. dimer, trimer, tetramer or oligomer). An exemplary trimeric webbed antigenic immunogen of rgp140 and $M9_3$ is schematically depicted in FIG. 5. Note that the cytoplasmic tail is not present in the gp41 moiety of the rgp140 molecule; the disulphide loop is, however, present.
3. Likewise, admixtures containing rgp120 and an M9 derivative (i.e. dimer, trimer, tetramer or oligomer) may be formed. An exemplary trimeric webbed antigenic immunogen of rgp120 and $M9_3$ is schematically depicted in FIG. 6. Note that the gp41 moiety is not present in rgp120.

Figure 7:
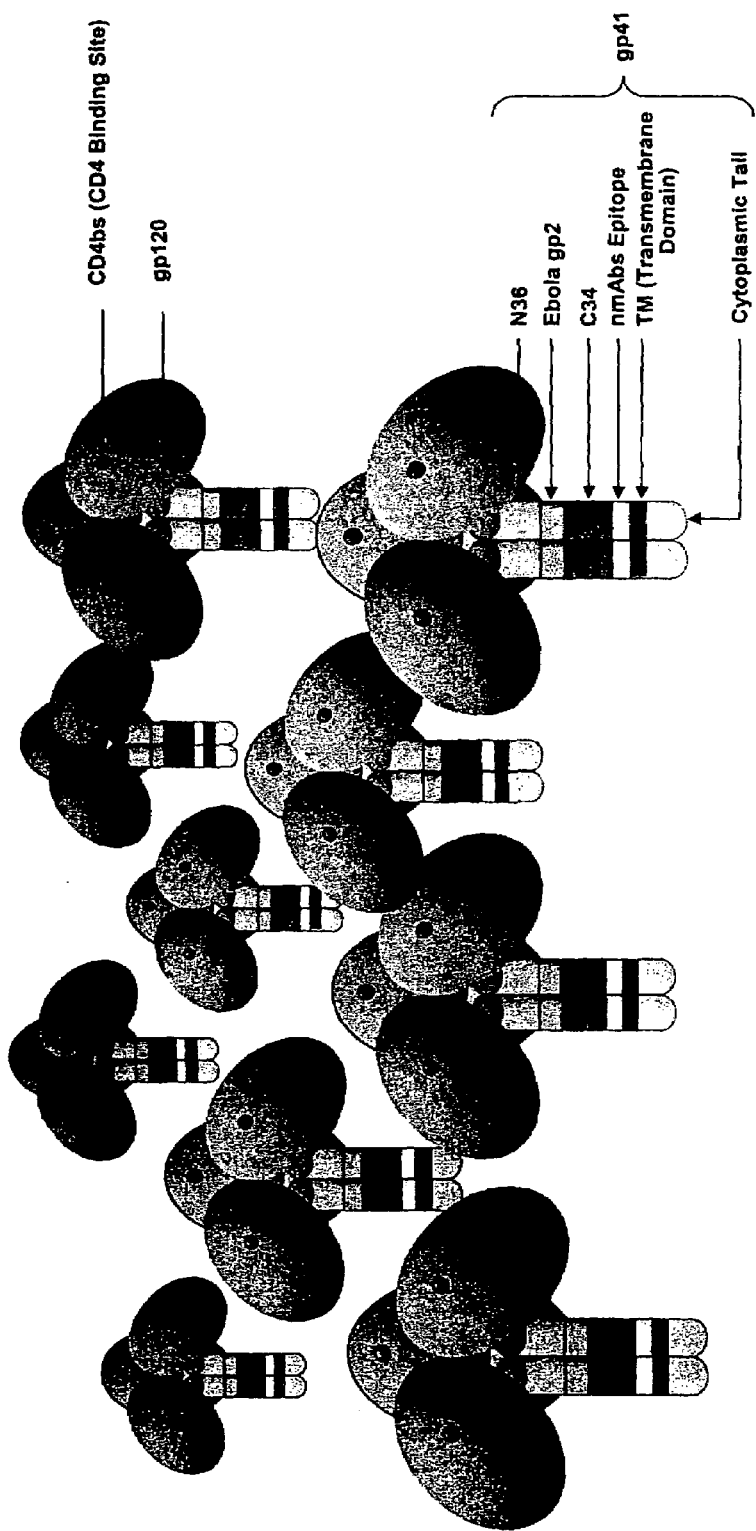
FIG. 7. Schematic representation of rgp $160_3$.
Figure 8:
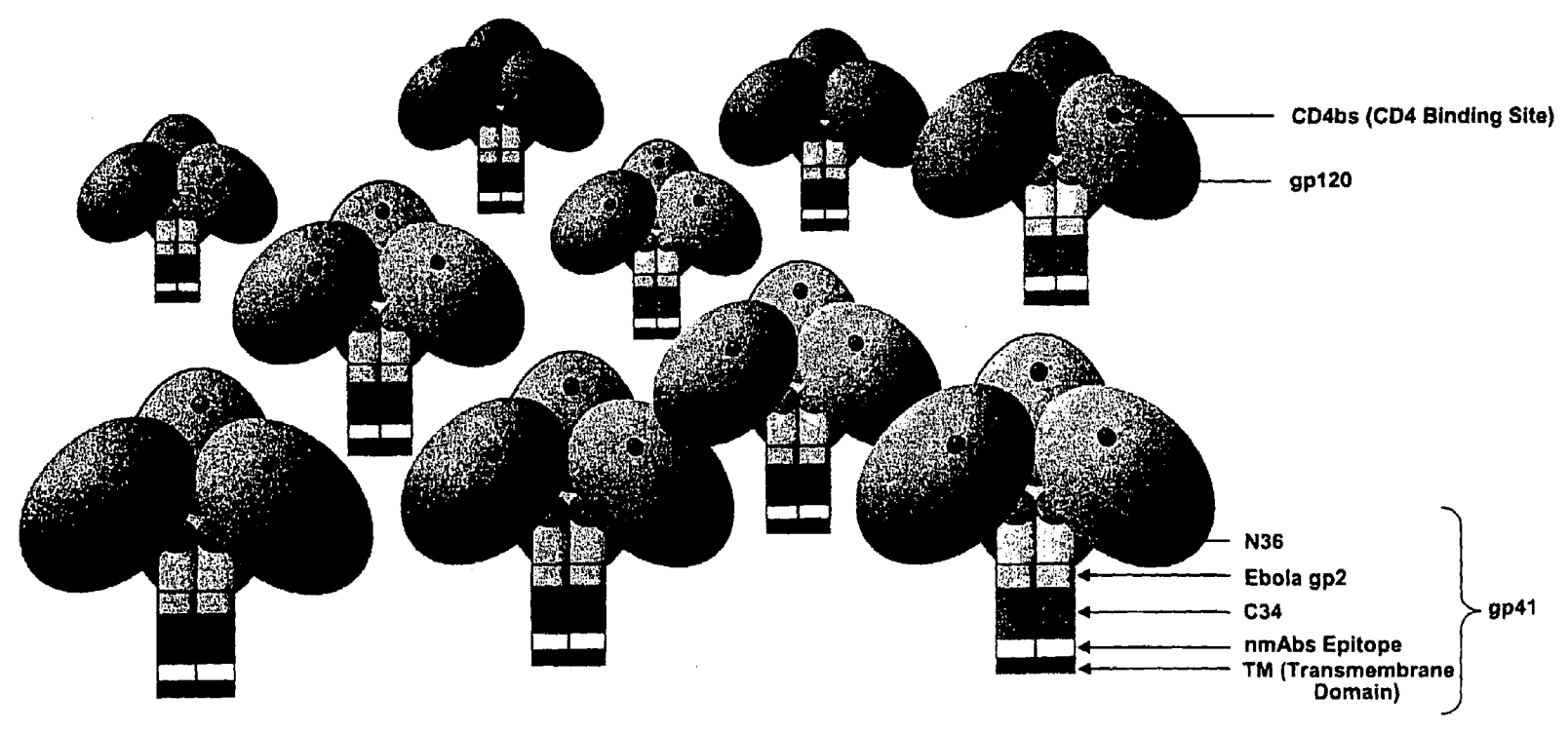

The exemplary webbed immunogens depicted in FIGS. 4, 5, and 6, are formed from a mixture of a monomeric form of an Env immunogen or derivative thereof, (e.g. monomeric rgp160, rgp140 and rgp120). However, in a preferred embodiment of the invention, webbed immunogens are formed from a combination of Env immunogens that are primarily trimeric even in the absence of an M9 derivative. The formation of such trimers can be induced by, for example, replacing the disulfide loop of the gp41 moiety of the molecule with the gp2 amino acid sequence of Ebola virus, as is discussed in detail below. For example, a schematic representation of trimeric rgp160 (herein referred to as $rgp160_3$ or $Env_3$; Farzan et al., J. Virol. 72: 7620 (1998)) is presented in FIG. 7. A schematic illustration of trimeric rgp140 (Binley et al., J. Virol. 74: 627 (2000); Yang et al., J. Virol. 74: 5716 (2000); Yang et al., J. Virol. 74: 4746 (2000)), herein referred to as rgp1403, is depicted in FIG. 8. As is the case with monomeric Env species, admixtures of the trimeric Env species and M9 derivatives result in aggregation and the formation of webbed immunogens. The webbed immunogens display native Env epitopes multivalently, and stabilize the interaction between B cells and the webbed immunogen resulting in surprising immunogenicity. It is noted that trimeric versions of rgp120 cannot be made in this manner due to the complete absence of a gp41 moiety from rgp120.

The following are descriptions of such webbed immunogens:

A preferred embodiment is comprised of admixtures containing trimeric rgp160 (i.e. $rgp160_3$ or $Env_3$) and an M9 derivative (i.e. dimer, trimer, tetramer or oligomer; such as $M9_3$. The resultant webbed immunogen is depicted schematically in FIG. 9. Note the presence of the Ebola gp2 sequence, and the cytoplasmic tail on the gp41 moiety.

Figure 10:
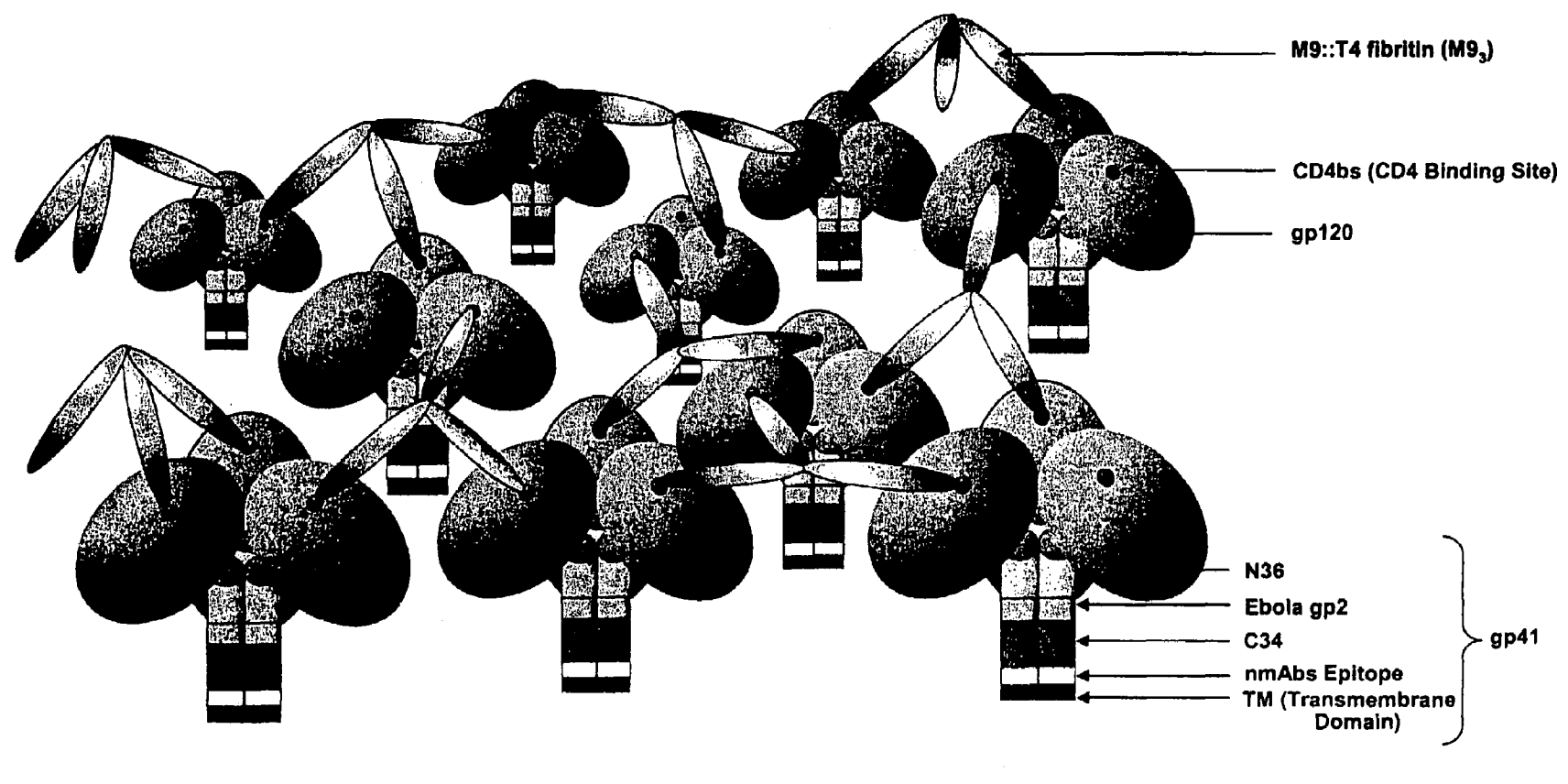

Another preferred embodiment is comprised of admixtures containing trimeric gp140 ($gp140_3$) and an M9 derivative (i.e. dimer, trimer, tetramer or oligomer). The resultant webbed immunogen is depicted schematically in FIG. 10. Note the presence of the Ebola gp2 sequence, and the absence of a cytoplasmic tail on the gp41 moiety.

The formation of webbed immunogens achieves three objectives:
(i) To conformationally constrain rgp160, rgp140 and rgp120, thereby exposing CD4i epitopes (Pal et al., Virology. 194: 833 (1993); Devico et al., Virology. 218: 258 (1996));
(ii) To display native tertiary structures of envelope on HIV; and
(iii) To increase the valence of conserved Env epitopes.

The preferred M9 derivative used in the present invention is a genetic fusion of the M9 domain of scorpion toxin (Vita et al., Proc. Natl. Acad. Sci. USA 96: 13091 (1999); Martin et al., Nature Biotech. 21: 71 (2003)) with a peptide that promotes the formation of dimers, trimers, tetramers or oligomers (FIG. 13).

The particular peptide that results in the formation of dimeric M9 is not important to the present invention and includes, but not restricted to, the Fc domain of murine (GenBank accession no. NM207603), non-human primate (GenBank accession no. NM001009077) or human (GenBank accession no. NM004107) IgG, the Fc domain of murine (GenBank accession no. AJ8333577), non-human primate (GenBank accession no. AB013766) or human (GenBank accession no. NM032029) IgA or the dimeric motif of the tobacco mosaic virus movement protein (Brill et al., J. Virol. 78: 3372; (2004)).

The particular peptide that results in the formation of trimeric M9 ($M9_3$) is not important to the present invention and includes, but not restricted to, the trimeric motif of bacteriophage T4 fibritin or GCN4, both of which induce trimerization of fusion partners (Yang et al., J. Virol. 74: 5716 (2000); Yang et al., J. Virol. 74: 4746 (2000); Yang et al., J. Virol. 76: 4634 (2002)).

The particular peptide that results in the formation of tetrameric M9 is not important to the present invention and includes, but not restricted to, the tetrameric cis-muconate lactonizing enzyme (CMLE; E.C. 5.5.1.5) from *Neurospora crassa* (Glumoff et al., Acta Crystallogr D Biol Crystallogr. 52: 221 (1996)).

The particular peptide that results in the formation of oligomeric M9 is not important to the present invention and includes, but not restricted to, the pentameric B subunit of cholera toxin (Zhang et al., J Mol. Biol. 251: 550 (1995)).

For convenience, the M9 multimer may include a tag, such as the His tag sequence from pETDuet-1 (Novagen, Madison, Wis.), which serves as a reporter that is useful in protein purification and SDS-PAGE analysis.

The particular Env used in the present invention is not important and includes, but is not restricted to, subtype A Env such as 98BRRS058 (GenBank accession no. AAL62002) and 99UGA07072 (GenBank accession no. AAN73453); subtype B Env such as KR5086 (GenBank accession no CAD10143) and BaL (GenBank accession no AAT67504); subtype C Env such as 99ET3 (GenBank accession no AAP76563) and C.ZA.1184 MB (GenBank accession no AAS98765), subtype D such as 99TCD.MN011 (GenBank accession no CAD58641) and 99UGA08483 (GenBank accession no AAP76515); subtype E such as 93JP-NH1 (GenBank accession no BAB55914) and NH2 (GenBank accession no BAA85017); subtype J such as SE9173 (GenBank accession no AAD17768) and SE9280 (GenBank accession no AAD17761); clade G Env such as 01 CM.4049HAN (GenBank accession no AAR21899) and 99NG869 (GenBank accession no AAM51932).

As indicated, webbed immunogens can be produced from full-length Env (rgp160) or truncated derivatives thereof, such as rgp120 (McKeating et al., J. Virol 67, 4932 (1993); Robey et al., Proc. Natl. Acad. Sci. USA 83: 7023 (1986)) or rgp140 (Binley et al., J. Virol. 74: 627 (2000); Yang et al., J. Virol. 74: 5716 (2000); Yang et al., J. Virol. 74: 4746 (2000)). In a preferred embodiment, webbed immunogens are formed from trimeric Env or trimeric rgp140 (Farzan et al., J. Virol. 72: 7620 (1998); Yang et al., J. Virol. 74: 5716 (2000); Yang et al., J. Virol. 74: 4746 (2000)).

FIG. 11 illustrates native HIV-1 gp41, containing fusion protein (FP), residue N36, disulfide loop S—S, residue C34, nmAb epitope, the transmembrane region (TM); and a modified chimeric form of gp41 used in the practice of the present invention. As can be seen, to promote stable trimerization of Env and rgp140, the following modifications were made:
  (i) The gp41 portion of the webbed immunogen was modified by deleting the amino-terminal fusion protein (FP) (Chan et al., Cell 89: 263 (1997)) and the immunodominant disulfide loop (S—S) located between N36 and C34, the heptad repeat domains of gp41 that are responsible for formation of a coiled-coil trimeric structure.
  (ii) The deleted disulfide loop was replaced with the heptad repeat domain of Ebola virus gp2, residues 552-593 of Zaire subtype (Sanchez et al., Virus Res 29: 215-240 (1993)) (FIG. 11). Gp2 is the membrane fusion protein of Ebola virus envelope, is anchored in the viral membrane, is highly α-helical, forms a coiled-coil and is thus trimeric, and is highly thermostable (Weissenhorn et al., Proc. Natl. Acad. Sci. 95: 6032 (1998)). The a and d positions of gp2 heptad repeat were fused in frame with those of N36 and C34 so that the heptad repeat was continuous. Notice that the C terminal portion of gp41 that contains the epitopes of known nmAbs 2F5, 4E10, and Z13 and the transmembrane domain TM were retained. This configuration of the immunogen is therefore membrane bound. However, the cytoplasmic tail was not retained in the modified form.
  (iii) To stabilize the noncovalent gp120-gp41 interaction, the following modifications (not shown) were introduced between gp120 and gp41: (i) the proteolytic cleavage site between gp120 and gp41 was mutated (REK/R to REK/T) and; (ii) a rigid linker consisting of the residues PSSP was introduced.

In one embodiment of the invention, the M9 domain of scorpion toxin is fused to a peptide that promotes trimerization. The particular peptide is not important to the present invention and includes, but not restricted to, the trimeric motif of bacteriophage T4 fibritin and GCN4, which induces trimerization of fusion partners (Yang et al., 2000; 2000a; 2002). For convenience $M9_3$ can include a tag to serve as a reporter, such as the His tag sequence from pETDuet-1 (Novagen, Madison, Wis.).

To facilitate secretion from mammalian cells, the polynucleotide sequences encoding $Env_3$, $rgp140_3$, Env, rgp140, rgp120 and the M9 derivative may include a leader sequence, such as the human tissue plasminogen activator signal peptide (GenBank accession no. E02331). The particular signal peptide employed is not critical and may be obtained instead from human interferon (GenBank accession no. CAC80088), human chromogranin A (GenBank accession no. NP001266), human casein beta (GenBank accession no. NP001882), tumor rejection antigen-1, gp96 (GenBank accession no. NP003290), and human zona pellucida glycoprotein 2 preprotein (GenBank accession no. NP003451)

When $Env_3$, $rgp140_3$, Env, rgp140, or rgp120 are mixed with the M9 derivative, e.g. $M9_3$, the M9 derivative crosslinks two or more $Env_3$, $rgp140_3$, Env, rgp140, or rgp120 molecules, thereby creating aggregates (FIGS. 4-6 and 9-10). This aggregation results in the formation of multivalent epitopes and augments the immunogenicity of the epitopes for humoral immune responses.

The particular ratio of $Env_3$:M9 derivative, $rgp140_3$:M9 derivative, Env:M9 derivative, or rgp120:M9 derivative in webbed immunogens is not important to the present invention and can be in the range of about 0.01-100:1. In a preferred embodiment, the ratio is about 0.1-10:1. In another preferred embodiment, the ratio is 1:1.

Construction of Webbed HIV-1 Envelope Immunogen

The recombinant DNA procedures used in the construction of webbed immunogens, including PCR, restriction endonuclease (herein referred to as "RE") digestions, DNA ligation, agarose gel electrophoresis, DNA purification, and dideoxynucleotide sequencing, are described elsewhere (Miller, *A Short Course in Bacterial Genetics*, Cold Spring Harbor Laboratory Press, Cold Spring Harbor, N.Y.; (1992); Sambrook et al., *Molecular Cloning: A Laboratory Manual*, Cold Spring Harbor Laboratory Press, Cold Spring Harbor, N.Y.; 1992)). Bacterial transformation methods employed standard techniques such as electroporation and physical transformation techniques (Miller, *A Short Course in Bacterial Genetics*, Cold Spring Harbor Laboratory Press, Cold Spring Harbor, N.Y.; (1992); Sambrook et al., *Molecular Cloning: A Laboratory Manual*, Cold Spring Harbor Laboratory Press, Cold Spring Harbor, N.Y.; 1992)).

Sequences encoding the components of webbed immunogen can be purchased from commercial sources that offer synthetic DNA on a fee-for-service basis, such as GenScript Corp, Piscataway, N.J., or Midland Certified Reagent Co., Midland, Tex. Alternatively, gene sequences can be made synthetically using an Applied Biosystems ABI™ 3900 High-Throughput DNA Synthesizer (Foster City, Calif. 94404 U.S.A.) and procedures provided by the manufacturer. To synthesize large sequences, i.e. greater than 200 bp, a series of segments of the full-length sequence are generated by PCR and ligated together to form the full-length sequence using procedures well know in the art. However, smaller sequences, i.e. those smaller than 200 bp, can be made synthetically in a single round using an Applied Biosystems ABI™ 3900 High-Throughput DNA Synthesizer (Foster City, Calif. 94404 U.S.A.) and procedures provided by the manufacturer.

Polynucleotide sequences described herein encoding the components of the webbed imunogen can be inserted into a vector to enable propagation of said sequences or expression of said webbed immunogens in cells. The term "vector" herein refers to a plasmid, virus, recombinant double stranded RNA phage (rdsRP; see, e.g. US patent application no. 20040132678) or other vehicle that can be altered by insertion or incorporation of said sequences. Such vectors can be used for genetic manipulation (i.e., "cloning vectors") or can be used to transcribe or translate the inserted polynucleotide (i.e., "expression vectors"). In the latter instance, control elements, including promoters present within an expression vector, are included to facilitate proper transcription and translation (e.g., splicing signal for introns, maintenance of the correct reading frame of the gene to permit in-frame translation of mRNA and stop codons). In vivo or in vitro expression of the polynucleotides described herein can be conferred by a promoter operationally linked to polynucleotide sequences described herein encoding $Env_3$, $rgp140_3$, Env, rgp140, or rgp120 and the M9 derivative. "Promoter" refers to a minimal nucleic acid sequence sufficient to direct transcription of the polynucleotide sequences described herein encoding Env$_3$, rgp140$_3$, Env, rgp140, or rgp120 and the M9 derivative.

Examples of plasmid vectors that can be used to clone and/or express $Env_3$, $rgp140_3$, Env, rgp140, or rgp120 and the M9 derivative include pBR322 (ATCC# 31344); pUC19 (ATCC# 37254); pcDNA3.$1_{ZEO}$ (Invitrogen, Carlsbad Calif. 92008; Cat. NO. V385-20; DNA sequence available at the Invitrogen website. pNGVL (National Gene Vector Laboratory, University of Michigan, MI); p414cyc (ATCC# 87380), p414GALS (ATCC# 87344), pBAD18 (ATCC# 87393), pBLCAT5 (ATCC# 77412), pBluescriptIIKS, (ATCC# 87047), pBSL130 (ATCC# 87145), pCM182 (ATCC# 87656), pCMVtkLUC (ATCC# 87633), pECV25 (ATCC#77187), pGEM-7zf (ATCC# 87048), pGEX-KN (ATCC# 77332), pJC20 (ATCC# 87113, pUB110 (ATCC# 37015), pUB18 (ATCC# 37253).

Vectors based on bovine papilloma virus (BPV) have the ability to replicate as extra-chromosomal elements (Sarver et al., Mol. Cell. Biol., 1:486 (1981)). Shortly after entry of an extra-chromosomal vector into mouse cells, the vector replicates to about 100 to 200 copies per cell. Because transcription of the inserted cDNA does not require integration of the plasmid into the host's chromosome, a high level of expression occurs. Such vectors also have been employed in gene therapy (U.S. Pat. No. 5,719,054 to Boursnell et al., the entire contents of which is hereby incorporated by reference). CMV-based vectors also are included (U.S. Pat. No. 5,561,063 to Hock et al., the entire contents of which is hereby incorporated by reference).

Examples of promoters that have been used to express webbed immunogens include the SV40 early promoter (Genebank accession # M99358, Fiers et al., Nature, 273: 113-120 (1978)), the cytomegalovirus immediate early promoter/enhancer (Genebank accession # AF025843) and the rous sarcoma virus long terminal repeat (Genebank accession # M83237; Lon et al., Hum. Immunol., 31: 229-235 (1991)) promoters, or the eukaryotic promoters or parts thereof, such as the β-casein (Genebank accession # AF194986; ref Fan et al., Direct submission (2000)), uteroglobin (Genebank accession # NM003357; ref Hay et al., Am. J. Physiol., 268: 565-575 (1995)), β-actin (Genebank accession # NM0010101; ref Vandekerckhove and Weber. Proc. Natl. Acad. Sci. U.S.A., 73: 1106-1110 (1978)), ubiquitin (Genebank accession # AJ243268; Robinson. Direct Submission, (2000)) or tyrosinase (Genebank accession # NM000372; Shibaharo et al., Tohoku J. Exp. Med., 156: 403-414 (1988)) promoters.

Another object of the present invention is to provide recombinant viruses or viral vectors that direct expression of webbed immunogens. For example, when using adenovirus expression vectors, the nucleic acid sequence may be inserted into an adenovirus transcription/translation control complex, e.g., the late promoter and tripartite leader sequence. Alternatively, the vaccinia virus 7.5K promoter may be used. Methods for constructing and producing said viral vectors are well known to those skilled in the art (Mackett et al., Proc. Natl. Acad. Sci. USA, 79:7415-7419 (1982); Mackett et al., J. Virol., 49:857 (1984); Panicali et al., Proc. Natl. Acad. Sci. USA, 79:4927 (1982); Girard et al., C R Acad Sci III., 322: 959 (1999); B. Moss et al., AIDS, 2 Suppl 1:S103 (1988)). The expression of webbed immunogens is not limited to the aforementioned viral vectors and can be accomplished in viral vectors such as, but not limited to adenoviral vectors (U.S. Pat. No. 5,700,470 to Saito et al., the entire contents of which is hereby incorporated by reference and U.S. Pat. No. 5,731,172 to Saito et al., the entire contents of which is hereby incorporated by reference), adeno-associated vectors (U.S. Pat. No. 5,604,090 to Alexander et al., the entire contents of which is hereby incorporated by reference), herpes simplex virus vectors (U.S. Pat. No. 5,501,979 to Geller, the entire contents of which is hereby incorporated by reference), semliki-forest virus (Girard et al., C R Acad Sci III., 322:959 (1999); Mossman et al., J. Virol., 70:1953 (1996)) and retroviral vectors (U.S. Pat. Nos. 5,624,820; 5,674,703; and 5,693,508, to Cooper, Woo et al. and Chang, respectively, the entire contents of which are hereby incorporated by reference, and WIPO publications WO92/05266 and WO92/14829).

Yet another object of the present invention is to provide expression systems that utilize nucleic acid vaccines (Andre et al., J. Virol. 72:1497 (1998); Mulligan and Webber AIDS 13 suppl A, S105 (1999); O'Hagan et al., J. Virol. 75: 9037 (2001); Rainczuk et al., Infect Immun. 72:5565 (2004)). The particular vector backbone of the nucleic acid vaccine in which sequences encoding $Env_3$, $gp140_3$, Env, gp140, or gp120 and the M9 derivative are inserted is not important to the present invention and includes, but is not restricted to, pcDNA3.$1_{ZEO}$ and pVAX1 (Invitrogen, Carlsbad, Calif. 92008; Cat. No. V385-20 and V260-20, respectively; DNA sequence available at the Invitrogen website; pNGVL (National Gene Vector Laboratory, University of Michigan, MI); p414cyc (ATCC# 87380), p414GALS (ATCC# 87344).

The design, application, and immunology of DNA vaccines has been reviewed elsewhere (Donnelly et al., Annu Rev Immunol. 15:617 (1997); Robinson and Pertmer Adv Virus Res 55:1 (2000); Gurunathan et al., Annu. Rev. Immunol 18:927 (2000); Ulmer, Curr Opin Drug Discov Devel. 4:192 (2001)). Briefly, DNA vaccines are configured to direct the in vivo expression of a foreign gene (the immunogen) in the vaccine recipient and, consequently, to induce protection against challenge with the pathogen (Ulmer et al., Science 259: 1745 (1993); Robinson et al., Vaccine 11:957 (1993)). Typically, the foreign gene is cloned into a bacterial plasmid that is optimized for expression in eukaryotes and consists of the following: (i) an origin of replication for propagation in bacteria; usually an *E. coli* origin such as ColEI is used; (ii) an antibiotic resistance gene, usually kanamycin, for selection of the plasmid in bacteria; (iii) a strong promoter for optimal expression in mammalian cells—cytomegalovirus (CMV) or simian virus 40 (SV40) are typically used; (iv) multiple cloning site downstream of the promoter for insertion of the gene of interest; and (v) SV40 or bovine growth hormone (BGH) polyadenylation signal for stabilization of mRNA.

Still another object of the present invention is to deliver vectors utilizing non-pathogenic or attenuated bacterial strains harboring plasmids capable of expressing webbed immunogens, such as, but not restricted to *Escherichia* spp., *Salmonella* spp., *Shigella* spp., *Mycobacterium* spp., and *Listeria* spp.

The particular *Escherichia* strain employed is not critical to the present invention. Examples of *Escherichia* strains which can be employed in the present invention include *Escherichia coli* strains DH5a, HB 101, HS-4, 4608-58, 1184-68, 53638-C-17, 13-80, and 6-81 (Sambrook et al., supra; Grant et al., supra; Sansonetti et al., Ann. Microbiol. (Inst. Pasteur), 132A:351 (1982)), enterotoxigenic *E. coli* (Evans et al., Infect. Immun., 12:656 (1975)), enteropathogenic *E. coli* (Donnenberg et al., J. Infect. Dis., 169:831 (1994)) and enterohemorrhagic *E. coli* (McKee and O'Brien, Infect. Immun., 63:2070 (1995)).

The particular *Salmonella* strain employed is not critical to the present invention. Examples of *Salmonella* strains that can be employed in the present invention include *S. typhi* (ATCC No. 7251), *S. typhimurium* (ATCC No. 13311), *Salmonella galinarum* (ATCC No. 9184), *Salmonella enteriditis*

(ATCC No. 4931) and *Salmonella typhimurium* (ATCC No. 6994). *S. typhi* aroC, aroD double mutant (Hone et al., Vacc., 9:810-816 (1991)), *S. typhimurium* aroA mutant (Mastroeni et al., Micro. Pathol., 13:477-491 (1992)).

The particular *Shigella* strain employed is not critical to the present invention. Examples of *Shigella* strains that can be employed in the present invention include *Shigella flexneri* (ATCC No. 29903), *Shigella flexneri* CVD1203 (ATCC No. 55556), *Shigella flexneri* 15D (Sizemore et al., Vaccine 15: 804 (1997) and Sizemore et al., Science 270: 299 (1995)), *Shigella sonnei* (ATCC No. 29930), and *Shigella dysenteriae* (ATCC No. 13313).

The particular *Mycobacterium* strain employed is not critical to the present invention. Examples of *Mycobacterium* strains that can be employed in the present invention include *M. tuberculosis* CDC1551 strain (Griffith et al., Am. J. Respir. Crit. Care Med. 152: 808 (1995)), *M. tuberculosis* Beijing strain (van Soolingen et al., J Clin Microbiol 33:3234 (1995)) H37Rv strain (ATCC#:25618), *M. tuberculosis* pantothenate auxotroph strain (Sambandamurthy, Nat. Med. 8: 1171 (2002), *M. tuberculosis* rpoV mutant strain (Collins et al., Proc Natl Acad Sci USA. 92: 8036 (1995)), *M tuberculosis* leucine auxotroph strain (Hondalus et al., Infect. Immun. 68(5): 2888(2000)), BCG Danish strain (ATCC # 35733), BCG Japanese strain (ATCC # 35737), BCG, Chicago strain (ATCC # 27289), BCG Copenhagen strain (ATCC #: 27290), BCG Pasteur strain (ATCC #: 35734), BCG Glaxo strain (ATCC #: 35741), BCG Connaught strain (ATCC # 35745), BCG Montreal (ATCC # 35746).

The particular *Listeria* strain employed is not critical to the present invention. Examples of *Listeria monocytogenes* strains which can be employed in the present invention include, but not restricted to, *L. monocytogenes* strain 10403S (e.g. Stevens et al., J Virol 78: 8210 (2004)), *Listeria ivanovii* and *Listeria seeligeri* strains (Haas et al., Biochim. Biophys. Acta. 1130:81 (1992)) or mutant *L. monocytogenes* strains such as (i) actA plcB double mutant (Peters et al., FEMS Immunology and Medical Microbiology 35: 243 (2003)); Angelakopoulous et al., Infect and Immunity 70: 3592 (2002.)); (ii) dal dat double mutant for alanine racemase gene and D-amino acid aminotransferase gene (Thompson et al., Infect and Immunity 66: 3552 (1998)).

Methods for delivering vectors using said bacterial vehicles are well known in the art (Powell et al., In: Molecular Approaches to the Control of Infectious Diseases, pp. 183-187, F. Bran, E. Norrby, D. Burton, and J. Meckalanos (eds), Cold Spring Harbor Press, Cold Spring Harbor, N.Y. (1996); Shata et al., Mol Med Today, 6:66-71 (2000); Hone and Shata, J. Virol. 75: 9665 (2001); Shata et al., Vaccine 20: 623 (2001); U.S. Pat. Nos. 6,500,419, 6,150,170, 5,877,159 and 5,824,538; Rapp and Kaufmann, Int. Immunol., 16:597 (2004); Dietrich et al., Curr. Opin. Mol. Ther. 5:10 (2003); Gentschev et al., J Biotechnol., 83:19 (2000))

The type of plasmid delivered by said bacterial vehicles for expression of polynucleotides encoding said webbed immunogens in target cells or tissues is not important to the present invention and include plasmids with sequences encoding $Env_3$, $gp140_3$, Env, gp140, or gp120 and the M9 derivative inserted in expression vectors such as, but not restricted to, pcDNA3.1$_{ZEO}$ (Invitrogen, Carlsbad Calif. 92008; Cat. NO. V385-20; DNA sequence available at the Invitrogen website; pNGVL (National Gene Vector Laboratory, University of Michigan, Ann Arbor, Mich.); p414cyc (ATCC# 87380), p414GALS (ATCC# 87344).

A further object of the present invention is to provide expression systems that utilize yeast expression systems. For expression in yeast a number of vectors containing constitutive or inducible promoters may be used (see, e.g., Current Protocols in Molecular Biology, Vol. 2, Ch. 13, ed. Ausubel et al., Greene Publish. Assoc. & Wiley Interscience (1988); Grant et al., "Expression and Secretion Vectors for Yeast," in Methods in Enzymology, Vol. 153, pp. 516-544, eds. Wu & Grossman, 3 1987, Acad. Press, N.Y. (1987); Glover, DNA Cloning, Vol. II, Ch. 3, IRL Press, Wash., D.C. (1986); Bitter, "Heterologous Gene Expression in Yeast," Methods in Enzymology, Vol. 152, pp. 673-684, eds. Berger & Kimmel, Acad. Press, N.Y. (1987); and The Molecular Biology of the Yeast *Saccharomyces*, eds. Strathem et al., Cold Spring Harbor Press, Vols. I and II (1982)). A constitutive promoter, such as ADH or LEU2, or an inducible promoter, such as GAL, may be used ("Cloning in Yeast," R. Rothstein, In: DNA Cloning, A Practical Approach, Vol. 11, Ch. 3, ed. D. M. Glover, IRL Press, Wash., D.C. (1986)).

A distinguishing feature of webbed immunogens is that the M9 derivative is expressed as a separate molecule. However, in another embodiment the webbed immunogen can be expressed as a single polypeptide as outlined in US patent application 2002/0,155,121 (Virus Coat Protein/Receptor Chimeras and Methods of Use), the complete contents of which are hereby incorporated by reference.

The expression of the webbed immunogen components (i.e. $Env_3$: M9 derivative, $rgp140_3$: M9 derivative, Env: M9 derivative, rgp140: M9 derivative or rgp120: M9 derivative) can be achieved using two separate vectors or both components may be assembled onto a single expression vector. In the latter instance, an internal ribosome-binding site (IRES) is included between the two components thereby creating a bicistronic expression cassette. The particular IRES employed in the present invention is not critical and includes, but not restricted to, IRES sequences on plasmid pIRES2-EGFP (Clontech Palo Alto, Calif.) obtained by PCR using primers specific for the 5' and 3' ends of the IRES located at nucleotides 665-1251 in pIRES2-EGFP, plasmid pIRES-EGFP can be obtained from the manufacturer (clontech.com/techinfo/vectors/vectorsF-1/pdf/pIRES-EGFPseq.pdf), plasmid pCITE4a (Novagen, Madison, Wis.; see also U.S. Pat. No. 4,937,190) by PCR using primers specific for the 5' and 3' ends of the CITE from nucleotides 16 to 518 in plasmid pCITE4a (the complete sequence of pCITE4a is available at the website (novagen.com/docs/NDIS/69913-000.HTM), plasmids pCITE4a-c (Novagen, URL novagen.com; U.S. Pat. No. 4,937,190); pSLIRES11 (Accession: AF171227; pPV (Accession # Y07702); pSVIRES-N (Accession #: AJ000156); Creancier et al., J. Cell Biol., 10: 275-281 (2000); Ramos and Mantinez-Sala, RNA, 10: 1374-1383 (1999); Morgan et al. Nucleic Acids Res., 20: 1293-1299 (1992); Tsukiyama-Kohara et al., J. Virol., 66: 1476-1483 (1992); Jang and Wimmer et al., Genes Dev., 4: 1560-1572 (1990)), or on the dicistronic retroviral vector (Accession #: D88622); or found in eukaryotic cells such as the fibroblast growth factor 2 IRES for stringent tissue-specific regulation (Creancier, et al., J. Cell. Biol., 150:275 (2000)), or the IRES of the 3'-untranslated region of the mRNA for the beta subunit of mitochondrial $H^+$-ATP synthase (Izquierdo and Cuezva, Biochem. J., 346:849 (2000)). The particular configuration of the bicistronic expression cassette is not important to the present invention, but in a preferred embodiment employs configurations that result in $M9_3$ being expressed in excess by placing the $Env_3$ sequence downstream of the IRES, i.e. NotI-$M9_3$—IRES-$Env_3$-NotI Recombinant plasmids carrying sequences encoding $Env_3$, $rgp140_3$, Env, rgp140, or rgp120 along with the M9 derivative are introduced into bacterial strains by electroporation using a BioRad Gene-Pulser set at 200Ω, 25 μF and 2.5 kV (BioRad Laboratories, Hercules, Calif.). Nucleotide sequencing is conducted to verify DNA sequences by standard automated sequencing techniques (Applied Biosystems automated sequencer, model 373A). DNA primers for DNA sequencing and polymerase chain reaction (herein referred to as "PCR") are synthesized using an Applied Biosystems ABI™ 3900 High-Throughput DNA Synthesizer (Foster City, Calif.).

Utility of Webbed Immunogens as Vaccines

The specific method used to formulate the webbed immunogens or vectors that express webbed immunogens (e.g. recombinant viruses, rdsRP and nucleic acid vaccines) described herein is not critical to the present invention and can be selected from a physiological buffer (Felgner et al., U.S. Pat. No. 5,589,466 (1996), the complete contents of which are hereby incorporated by reference); aluminum phosphate or aluminum hydroxyphosphate (e.g. Ulmer et al., Vaccine, 18:18 (2000)), monophosphoryl-lipid A (also referred to as MPL or MPLA; Schneerson et al., J. Immunol., 147: 2136-2140 (1991); e.g. Sasaki et al., Inf Immunol., 65: 3520-3528 (1997); Lodmell et al., Vaccine, 18: 1059-1066 (2000)), QS-21 saponin (e.g. Sasaki, et al., J. Virol., 72:4931 (1998); dexamethasone (e.g. Malone, et al., J. Biol. Chem. 269:29903 (1994); CpG DNA sequences (Davis et al., J. Immunol., 15:870 (1998); or lipopolysaccharide (LPS) antagonist (Hone et al., supra (1997)).

The webbed immunogen or vectors that express the same can be administered directly into animal tissues by intravenous, intramuscular, intradermal, intraperitoneal, intranasal and oral inoculation routes. The specific method used to introduce the webbed immunogen or vectors that express same into the target animal tissue is not critical to the present invention and can be selected from previously described vaccination procedures (see, e.g. Wolff, et al., *Biotechniques* 11:474-85 (1991); Johnston and Tang, Methods Cell Biol 43:353-365 (1994); Yang and Sun, *Nat Med* 1:481-483 (1995); Qiu, et al., *Gene Ther.* 3:262-8 (1996); Larsen, et al., *J. Virol.* 72:1704-8 (1998); Shata and Hone *J. Virol.* 75:9665-9670 (2001); Shata, et al., *Vaccine* 20:623-629 (2001); Ogra, et al., *J. Virol.* 71:3031-3038 (1997); Buge, et al., *J. Virol.* 71:8531-8541 (1997); Belyakov, et al., *Nat. Med.* 7, 1320-1326 (2001); Lambert, et al., *Vaccine* 19:3033-3042 (2001); Kaneko, et al., *Virology* 267: 8-16 (2000); Belyakov, et al., *Proc Natl Acad Sci USA* 96:4512-4517 (1999)).

The immunogenicity of webbed immunogen or vectors that express the same is assessed in an appropriate animal model (e.g. mice, rabbits guinea pigs or Rhesus macaques). Initially the webbed immunogen or vectors that express same are administered at dose appropriate to the formulation being used and are administered by an appropriate route, such as orally, intranasally, subcutaneously, or intramuscularly. The number of doses varies depending on the potency of the individual webbed immunogen or vectors that express the same and can be a single-, two-, three- or four-dose regimen spaced by 2- to 10-week intervals. Each immunogenicity study includes a negative control (e.g. ovalbumin or vectors that express the same; keyhole limpet hemaglutinin (KLH) or vectors that express the same) that does not contain or express a webbed immunogen.

To measure serum IgG and IgA responses invoked by the webbed immunogen, sera are collected 10, 20, 30, 40, 50, 60, 70, 80, 100, 200 and 365 days before and after vaccination. Blood is collected into individual tubes from the tail vein of each animal/human volunteer and allowed to clot by incubating for 4 hr on ice. After centrifugation in an appropriate size centrifuge (e.g. a microfuge for small samples and a Beckman Avanti 25i for large samples) for 5-30 min; the sera are transferred to fresh tubes and stored at −80° C. Mucosal IgG and IgA responses to antigens expressed by the genes of interest are determined using stools and vaginal washes that will be harvested before and regular intervals after vaccination. (Wu et al, Infect. Immun 63: 4933 (1995); Wu et al, AIDS Res. Hum. Retrovir 13:1187 (1997))_Standard ELISAs are used to quantitate the IgG and IgA responses to webbed immunogens and native structures on HIV-1 Env in the sera and mucosal samples. (Abacioglu et al, AIDS Res. Hum. Retrovir. 10:371 (1994); Pincus et al, AIDS Res. Hum. Retrovir. 12:1041 (1996)). Ovalbumin can be included in each ELISA as a negative control antigen. In addition, each ELISA can include a positive control serum, stool or vaginal wash sample, as appropriate. The positive control samples are harvested from animals vaccinated intranasally with 10 µg of the webbed immunogen mixed with 10 µg cholera toxin or sera harvested from HIV-infected individuals, as described (Bagley et al, Vaccine 21:3335 (2003)). The end-point titers are calculated by taking the inverse of the last serum dilution that produced an increase in the absorbance at 490 nm that is greater than the mean of the negative control row plus three standard error values.

To measure cellular immunity, cell suspensions of enriched CD4+ and CD8+ T cells from lymphoid tissues are used to measure antigen-specific T cell responses by cytokine-specific ELISPOT assay (Wu et al, Infect. Immun 63: 4933 (1995); Wu et al, AIDS Res. Hum. Retrovir 13:1187 (1997)). Such assays can assess the numbers of antigen-specific T cells that secrete IL-2, IL-4, IL-5, IL-6, IL-10 and IFN-γ. All ELISPOT assays are conducted using commercially-available capture and detection mAbs (R&D Systems and Pharmingen), as described (Wu et al, Infect. Immun 63: 4933 (1995); Wu et al, AIDS Res. Hum. Retrovir 13:1187 (1997); Shata et al, Vaccine 20: 623 (2001)). Each assay includes mitogen (Con A) and ovalbumin controls.

Production of Therapeutic Monoclonal Antibodies

Another object of the present invention is to provide monoclonal antibodies (herein referred to as "mAbs") that bind HIV-1 and are useful as therapeutics against this virus in humans. The particular animal in which the mAbs are derived is not important to the present invention and includes, but not limited to, mice, rats, macaques, chimpanzees, gorillas, goats and rabbits. In a preferred embodiment, the mAbs are derived from human B cells. Methods for making MAbs are well known to those skilled in the art (Harlow et al., Antibodies: A Laboratory Manual p. 726, eds. Cold Spring Harbor Pub. (1988)). Briefly, monoclonal antibodies can be obtained by injecting humans with a composition comprising or capable of expressing a webbed immunogen, verifying the presence of antibody production by analyzing sera from the vaccinated individuals, obtain B lymphocytes from peripheral blood lymphocytes or bone marrow, fusing the B lymphocytes with myeloma cells to produce hybridomas, cloning the hybridomas, selecting positive clones that produce mAbs to the webbed immunogen, and isolating the mAbs from the hybridoma cultures. The mAbs are isolated and purified from hybridoma cultures by a techniques well known to those skilled in the art, including, but not restricted to, affinity chromatography with protein-A sepharose, size-exclusion chromatography, and ion-exchange chromatography (see, e.g., Barnes et al., "Purification of Immunoglobulin G (IgG)," In: Methods in Molecular Biology, Vol. 10, pp. 79-104, Humana Press (1992) and Coligan et al., "Production of Polyclonal Antisera in Rabbits, Rats, Mice and Hamsters," In: Current Protocols in Immunology, Vol. 1, pp. 2.4.1, John Wiley and Sons, Inc. (2003)).

Unless specified otherwise, all terms used herein have the same meaning as terms understood by one skilled in the art to which this invention belongs. All publications, patent applications, patents, and other references mentioned herein are incorporated by reference in their entirety. Although suitable methods, materials and reagents are described herein that can be used to practice or test the present invention, methods, materials and reagents similar or equivalent to those described herein can be used to accomplish the same. The following examples are provided for illustrative purposes only, and are in no way intended to limit the scope of the present invention.

EXAMPLES

Example 1

Construction of Vectors that Express Webbed Immunogens

The webbed immunogen in this example is comprised of three major components:

1. M9::fibritin fusion (synthesized by GenScript Corp, Piscataway, N.J.);
2. rgp120 CRF A/G (synthesized by Midland Certified Reagent Co., Midland, Tex.); and
3. rgp41::Ebola gp2 chimera (synthesized by GenScript Corp, Piscataway, N.J.).

All three synthetic genes were cloned into pVAX1 (cat. # V260-20, Invitrogen, Carlsbad, Calif.) as follows: HindIII for M9::fibritin, BamHI and EcoRI for rgp120 CRF A/G, and rgp41::Ebola gp2 was cloned into EcoRI and NotI sites. To construct rgp140, rgp120 and rgp41::Ebola gp2 were fused to form a single expression cassette in the BamHI and NotI sites of pVAX1, in which there is a rigid linker between rgp120 and gp41::Ebola gp2 (Modular Genetics Inc., Woburn, Mass.). Consequently, the M9::fibritin construct is expressed from a separate cassette, and it has a His tag that serves as a reporter. Each of M9::fibritin and $rgp140_3$ has a human Tissue plasminogen activator leader sequence to facilitate secretion from mammalian cells. Schematic representations of the components of $rgp140_3$ and M9::T4 fibritin are given in FIG. 12 and FIG. 13, respectively.

Alternatively, all three components may be assembled onto a single plasmid as follows: NotI-M9::fibritin-CITE-rgp120-rigidlinker-gp41::gp2-NotI. Notice that a cap-independent translation enhancer (CITE) (from pCITE-4a(+), cat. # 69913-3, Novagen, Madison, Wis.) is placed immediately upstream of the rgp120 sequence.

Nucleotide sequence of all constructs was verified by standard automated dideoxy method.

Example 2

Purification of a DNA Vaccine that Expresses a Webbed Immunogen

Endotoxin-free DNA (<5 EU/mg plasmid) is employed in immunogenicity studies and may be obtained on a fee-for-service basis (Aldevron LLC, Fargo, N. Dak.). Briefly, each plasmid is transformed into either DH5-alpha competent cells at 37° C. or STBL4 competent cells at 30° C. The following morning, three individual colonies for each are picked and expanded in starter cultures. Samples taken from the starters at five hours are used to select the inoculum that is then used to spike 1-3 L of medium. Depending on the host strain, the cultures are grown in shake flasks (250 rpm, 30 or 37 C) for 14-20 hours. The biomass is washed with a low salt buffer, repacked by centrifugation and then processed with a standard alkaline lysis. The lysate is clarified by filtration and then subjected one or more rounds of anion exchange chromatography as required to bring the endotoxin level to <5 EU/mg. The plasmid is isolated from the elution buffer with 2-propanol precipitation and the pellet is washed with 70% ethanol, allowed to air-dry and then dissolved in the final buffer, usually PBS.

Each plasmid is precipitated onto 1 μm gold microcarriers and cartridges are prepared for vaccination with a Helios gene gun according to the manufacturer's protocol (Bio-Rad). A microcarrier loading quantity of 0.5 mg/dose and DNA loading ratio of 2 μg/mg gold may be used, so that the amount of DNA delivered per shot is 1 μg. Accordingly 50 mg of gold is weighed into a microcentrifuge tube and 100 μl of 0.05 M spermidine (cat #S4139-1G Sigma, St. Louis) is added. The mixture is vortex and sonicated 3-5 secto break up gold clumps. Subsequently, 100 μl of the plasmid is added to the gold and spermidine mixture and vortexed for about 5 sec. While vortexing, 100 μl of 1 M $CaCl_2$ is added dropwise to the mixture, and it is incubated at room temperature for 10 min. Next, the mixture is spun in a microcentrifuge for ~15 sec, and the supernatant is discarded. The pellet is vortexed to resuspend it in what is left of the supernatant and 1 ml of fresh 100% ethanol is added, spun ~5 sec, and the supernatant is discarded. The ethanol wash is performed three times. The pellet is then resuspended in 200 μl of 0.1 mg/ml Polyvinylpyrrolidone in 100% ethanol (hereafter referred to as PVP), and the solution is transferred to a 15 ml polypropylene tube. The microcentrifuge tube is given an additional rinse with 2001 μl of the PVP solution and added to the polypropylene tube. The gold-DNA mixture is suspended in a final volume of 6 ml PVP.

Subsequently, the gold-DNA mixture is loaded onto Gold-coat tubing using a Tubing prep station, according to manufacturer's instructions (Bio-Rad). Approximately 66 cm of Gold-coat tubing is loaded onto the prep station, and is dried by purging with nitrogen at a flow rate of 0.3-0.4 LPM for at least 15 min. The Gold-coat tubing is then inserted into one end of an adaptor tube, which, in turn, is fitted to a 10 cc syringe. The DNA-gold mixture is vortex and, using the syringe, about 3 ml is quickly drawn into the Gold-coat tubing, ensuring to avoid air bubbles and to leave about 17 cm of adaptor tube unfilled at each end. The mixture is allowed to settle for about 5 min, following which the ethanol is slowly removed using the syringe. The tubing is detached from the syringe, rotated 180° for about 5 sec while still in the groove of the Prep Station. The motor of the Prep Station is turned on to rotate the Station, and the gold is allowed to smear in the tube for ~30 sec. The nitrogen is turned on for 5 min at a rate of 0.35-0.4 LPM to dry the Gold-coat tubing. Finally, the nitrogen and motor are turned off, and the tubing is removed from the Prep Station.

The tubing is cut into ~1.2 cm pieces using a Tubing Cutter (BioRad). A storage vial containing a desiccant pellet is placed at the base of the Cutter. One end of the coated tubing is inserted all the way into the tubing channel until it makes contact with the rear plate of the Cutter. The handle of the Cutter is then pressed sharply, and the cut piece falls into the storage vial. The process of inserting and cutting is repeated until the entire length of usable tubing is cut into cartridges. The cartridges are thus ready for vaccination, and are stored at 4° C. until they are used.

Example 3

Creation of Cell Lines that Express Webbed Immunogens Expression, Purification, and Characterization of Webbed rgp140$_3$ Immunogen Transfection and Expression in Mammalian Cells To verify that webbed rgp140$_3$ immunogens are expressed in cells and form aggregates, cells are transfected with one or more vectors capable of producing rgp140$_3$ and M9$_3$. For stable expression of webbed immunogens, vectors (e.g. plasmids containing a selectable marker conferring resistance to a selective pressure, recombinant adenoviruses, plasmids containing viral origins of replication, or plasmids based on bovine papilloma virus (BPV) that have the ability to replicate as extra-chromosomal elements (Sarver et al., *Mol. Cell. Biol.*, 1:486 (1981)) in which the expression of rgp1403 and M9$_3$ are controlled by appropriate elements (e.g., promoters, enhancers, introns, transcription terminators, Kozak sequences, polyadenylation sites) can be introduced into a target cell or cell line. Stable maintenance of said vectors in cells may occur following integration of said vectors into the genomic DNA of the cells.

The particular cell or cell line used to express, either transiently or stably, rgp140$_3$ and M9$_3$, either separately or together, is not important to the present invention and includes but is not restricted to dendritic cells (ATCC No. CRL-2740), stem cells, such as CE-3 (ATCC No. SCRC-1039), Chinese hampster ovary (CHO) cells (ATCC No. CCL-61), HeLa cells (ATCC No. CCL-2), and 293 cells (ATCC No. CRL-1573).

The particular selection system used is not important to the present invention and includes but not restricted to the neomycin-resistance gene (Genbank accession no. AAC53629; Alexeyev et al., 1995 Gene 160: 63-67), the Zeocin-resistance gene (Genbank accession no. AAB00458; Calcutt and Schmidt Gene 151: 17 (1994)), the hygromycin gene (Genbank accession no. U89672; Rees et al., BioTechniques 20: 102 (1996); Santerre et al., Gene, 30:147 (1984)) trpB or hisD (Hartman et al., Proc. Natl. Acad. Sci. USA, 85:8047 (1988)); and the 2-(difluoromethyl)-DL-ornithine-(DFMO)-resistance gene encoding ornithine decarboxylase (Genbank no. NP438749; McConlogue, In: Current Communications in Molecular Biology, Cold Spring Harbor Laboratory, ed. (1987)).

Methods used to transform target cells or cell lines are not important to the present invention and may be carried out by conventional techniques known to those skilled in the art (e.g., calcium phosphate, microinjection, electroporation, and viral vectors). Similarly, the use of liposomes for introducing various polynucleotides expressing said webbed immunogens into cells is known to those of skill in the art (see, for example, U.S. Pat. No. 4,844,904 (Hamaguchi et al.), U.S. Pat. No. 5,000,959 (Iga et al), U.S. Pat. No. 4,863,740 (Kissel et al.) and U.S. Pat. No. 4,975,282 (Cullis et al), the entire contents of all of which are hereby incorporated by reference; Lee and Low, J. Biol. Chem., 269:198 (1994); Lee and Low Biochem. Biophys. Act, 1233:134 (1995)).

Upon transfection, the cells are initially grown without the selecting agent for 24-48 h, upon which fresh growth medium containing the appropriate selecting agent is added and the cells are grown for a further 24-48 h. Supernatants collected thereafter are tested for expression of Env$_3$ by assessing binding to polyclonal gp120 IgG in solid phase and capture ELISA (described in detail below). Stably transfected cells are stored in liquid nitrogen.

An immunoblot assay is also used to detect expression of both rgp140$_3$ and M9$_3$ in supernatants, in which case the later construct is tested for binding to His tag monoclonal antibody (cat# 70796-3, Novagen, Wis.). Briefly, samples are denatured by boiling for 10 min in 2% sodium dodecyl sulfate (SDS) and 1% β-mercaptoethanol, following which the samples are electrophoresed through a 4-20% polyacrylamide gradient gel. The bands are transferred to a nitrocellulose membrane by using an electroblotter (Owl, Portsmouth, N.H.). To prevent non-specific binding, the membrane is blocked by incubating at least 1 h in 5 percent blotto (nonfat dry milk resuspended in TBS). Protein detection is performed using rgp120-specific IgG and His-tag-specific antibody for rgp140$_3$ and M9$_3$, respectively. To remove unbound antibody, the membrane is washed four times with 0.1% Tween (prepared in TBS). For color development, the membrane is treated with peroxidase- or alkaline phosphatase-labeled secondary antibody (suspended in 5 percent blotto). Protein size is determined in comparison to size marker, and quantitation is performed in a Versadoc Imager (BioRad, Hercules, Calif.).

Purification of Webbed rgp1403 Immunogen

To purify webbed rgp140$_3$ immunogen, the culture supernatant is collected from transiently or stably transformed cells, as described above and rgp140$_3$ is purified by affinity chromatography using a human anti-gp120 mAb, such as A32, coupled to Sepharose 4B colums (Pierce, Rockford, Ill.). The columns are equilibrated with PBS before use, the supernatant is applied to the column for 24 hr using a peristaltic pump, and the flow through is collected. Bound portions are eluted with 0.2 M glycine pH 2.8 and then dialyzed overnight at 4° C. against PBS. Protein concentration is then determined by a BCA assay.

Antigenicity of the Purified Webbed rgp140$_3$ Immunogen

Given that M9 induces CD4-like conformational changes in gp120, CD4i epitopes will be exposed in webbed rgp140$_3$ immunogen. Exposure of such epitopes is assessed by testing binding of mAb against CD4i epitopes to the webbed rgp140$_3$ immunogen in a capture ELISA. Briefly, ELISA microtiter plates (Nunc, Rochester, N.Y.) are coated with 5 μg/mL affinity purified sheep anti-HIV-1 gp120 (Cliniqa, Fallbrook, Calif.) and incubated overnight at 4° C. Plates were washed four times with 0.05% Tween 20 in TBS, and then blocked at room temperature for 1 hr with blotto (5 percent non-fat dried milk in TBS). Plates are then washed with Tween solution, as above. Samples and controls are diluted in blotto before adding to plates to a total of 200 μl. Bound rgp140 is detected using CD4i mAbs such as, but not limited to 1.9E, 2.5E, and X5, each of which is diluted in blotto before application to plates. Plates are then washed as above, and alkaline phosphatase-conjugated secondary Ab diluted in blotto and 5% (v/v) neonatal ovine serum is added and incubated at room temperature for 1 h. Plates are washed four times and color is developed using the ELISA amplification system (Invitrogen, Carlsbad, Calif.). Absorbance is determined at 490 nm using a SpectraMax microplate spectrophotometer (Molecular Devices, Sunnyvale, Calif.).

Neutralization of HIV-1 by Purified Webbed rgp140$_3$ Immunogen

The ability of soluble webbed rgp140$_3$ immunogen to inhibit HIV-1 infection of mammalian cells in vitro is assessed. Neutralization assays employ U373/CD4/MAGI cells that express CCR5 or CXCR4 as targets, although other cell types such as peripheral blood mononuclear cells (PBMCs) are suitable. Approximately $5 \times 10^3$ cells per well in 100 µL culture medium are allowed to attach to 96-well flat bottom tissue culture plates by incubating overnight at 37° C. and 5% $CO_2$. Subsequently, the culture medium is discarded and replaced with flesh medium that contains 50 $TCID_{50}$ (tissue culture 50 percent infective dose) per well of HIV-1 and twofold serial dilutions of soluble webbed $rgp140_3$ immunogen and of commercially available purified gp120. As a control, infection is also allowed to proceed in the absence of webbed $rgp140_3$ immunogen. Neutralization of both primary and TCLA strains of HIV-is tested, and includes, but is not limited to the following: LAI, 92UG024, BaL, 89.6, various subtype A, CRF A/G, and C strains.

Infection is allowed to proceed for 24 h, after which the culture medium is replaced with fresh medium and the cells are incubated for 5-7 days. The cells are lysed and infectivity is assessed using a Galactostar chemiluminescent α-galactosidase assay (Applied Biosystems, Foster City, Calif.).

Structural Studies

To determine the structure of webbed $rgp140_3$ immunogen, a version that lacks the transmembrane domain is constructed. This truncated version is expressed in transiently or stably transfected 293 cells and purified as above. The purified protein is transferred to carbon film, stained, and examined by scanning electron microscopy to detect spike formation and trimer-trimer interactions.

Example 4

Purification of a Webbed Immunogen

Gel filtration chromatography is used to purify webbed $rgp140_3$ immunogen and controls to endotoxin-free levels suitable for immunogenicity studies. Gel filtration chromatography separates proteins in order of large to small molecules. Gel filtration may be used to separate proteins based on differences in their molecular size, or to remove low-molecular-weight contaminants such as salts, amino acids, and peptides. Standard protocols for gel filtration chromatography are described in Ausubel et al., (2003). Commercially available gel-filtration column containing a chromatographic matrix of defined pore size are used. The particular matrix employed is not critical to the present invention, and includes Sephadex, Sepharose, Sephacryl, Superose, Bio-Gel, and Bio-Sil. The matrix may be obtained preswollen in which case it is washed with gel-filtration buffer (Tris-HCl buffer, Sodium phosphate buffer, or Sodium acetate buffer with ionic strength of 0.05 M is normally used). The matrix is diluted, so that the slurry is 50 percent settled gel and 50 percent gel-filtration buffer. The slurry is then packed into a column. Next the separating volume of the column, the amount of liquid that will pass through the column from the point where large proteins begin to emerge to the point where small solutes are eluted, is determined. This is usually accomplished by running a void marker and obtaining the elution volume.

The protein sample is applied using a peristaltic pump, and proteins are subsequently eluted with an aqueous buffer, large proteins being generally eluted first. Individual chromatographic fractions thus collected and corresponding chromatograms are generated. The fractions are tested for binding to polyclonal or monoclonal HIV-1 IgG by ELISA and to His tag mAb.

The purified fractions thus obtained are prepared for vaccination of rabbits. 50 mcg of the purified webbed immunogen is admixed with 5 mcg cholera toxin (cat# 100, List Biological Laboratories, Campbell, Calif.) as adjuvant in a total volume of 250 ml. Cholera toxin is an oligomeric protein of MW 84 kDa and consists of a single A subunit surrounded by five B subunits. (Finkelstein, et al., J. Immun. 113, 145 (1974); Gill, Biochemistry 15, 1242 (1976); Lai J. Biol. Chem. 252, 7249 (1977)) It is a potent activator of adenylate cyclase and is the pathogenic agent responsible for the symptoms of cholera. The B subunit (choleragenoid) is responsible for the binding of the holotoxin to $G_{M1}$ ganglioside receptors on mammalian cell surfacs (van Heyningen, Nature 249, 415 (1974); Holmgren and Lonnroth J. Gen. Microbiol. 86, 49 (1975)) and facilitates entrance of the A subunit into the cell. The A subunit bears the ADP-ribosyl-transferase activity, which deregulates the $G_s$ protein causing activation of adenylate cyclase (van Heyningen and King Biochem. J. 146, 269 (1975)). Cholera toxin is therefore a powerful adjuvant due to its capacity to stimulate B-lymphocyte responses.

Example 5

Immunogenicity of Webbed Immunogens in Rabbits

The few known mAb against HIV-1 are peculiar in that they have unusually long (18-22 amino acid residues) third complementarity-determining region of the heavy chain (CDR H3) (Darbha et al, Biochemistry 43:1410 (2004); Saphire et al, Science 293:1155. (2001); Zwick et al, J. Virol. 78:3155 (2004)). The average length of CDR H3 in rabbits is ~11-12 and in mice is ~9-10 residues (Wu et al, Proteins 16:1 (1993)). Moreover, more sera per bleed can be obtained from rabbits than mice. For these reasons, immunogenicity studies are conducted in rabbits rather than mice.

The ability of webbed $rgp140_3$ immunogen to elicit a neutralizing antibody response is tested in a prime boost protocol by vaccinating rabbits with a Helios gene gun (BioRad, Hercules, Calif.). One hind leg of each rabbit is shaved prior to vaccination. Rabbits are primed on day 0 and boosted on day 14. Another boost, if necessary, may be given about day 60 after the prime.

To measure humoral responses to webbed $rgp140_3$, sera are collected before and at 10-day intervals after vaccination. About 2 ml of blood are collected into individual tubes from each rabbit's ear vein and allowed to clot by incubating for 4 hr on ice. After centrifugation in a microfuge for 5 min, the sera are transferred to fresh tubes and stored at −20° C. When appropriate (i.e. a given vaccine proves immunogenic in serum ELISA assays) mucosal IgG and IgA responses to webbed $rgp140_3$ are determined using fecal pellets and vaginal washes that are harvested before and 20, 30 and 40 days after vaccination (Wu et al, Infect. Immun 63: 4933 (1995); Wu et al, AIDS Res. Hum. Retrovir 13:1187 (1997)).

Capture and solid phase ELISAs, as described above, are utilized to quantitate IgG and IgA responses to webbed $rgp140_3$ in sera and mucosal samples. Purified soluble webbed $rgp140_3$ immunogen is suspended in PBS at a concentration of 3 μg/ml and is used to coat 96-well ELISA plates. Pre-immunization serum is included in each ELISA as a negative control. In addition, each ELISA includes a positive control serum, fecal pellet or vaginal wash sample, as appropriate. End-point titers are calculated by taking the inverse of the last serum dilution that produced an increase in the absorbance at 490 nm that is greater than the mean of the negative control row plus three standard error values.

Competition ELISA

To characterize the antigenic determinants of webbed $rgp140_3$ immunogen and controls, sera from immunized rabbits are tested for binding to purified soluble gp120 in competition with mAbs such as, but not limited to, 2.5E, 1.9E, 17b, X5, IgG1B12, 2G12, A32, and T3. The epitopes of 2.5E, 1.9E, 17b, and X5 are CD4i, and IgG1B12 binds to the CD4 binding site (CD4bs). The mAbs are usually biotinylated, so that reduction of absorbance ($OD_{490}$) is indicative of competition. Competition between immune sera and mAbs strongly suggests that the vaccine induces Abs to epitopes that at least overlap those of the mAbs.

Microtiter plates are coated with 5 μg/mL affinity purified sheep anti-HIV-1 gp120 (Cliniqa) and incubated overnight at 4° C. Plates are washed four times with the TBS-Tween solution described above. Plates are blocked with blotto, and capture achieved by applying a solution of 0.2 μg/mL soluble gp120 in 5% blotto and incubating at room temperature for 1 h. Plates are washed as described above, and threefold serial dilutions of serum, starting at 1:30, are applied in duplicate. Each MAb is then applied separately to the sera and incubated at room temperature for 1 h. Each MAb is tested for binding to soluble gp120 in the presence and absence of competing serum. Plates are washed and Peroxidase-labeled Streptavidin (KPL, Gaithersburg, Md.) diluted 1:300 in 5% blotto is added and incubated for 30 min at room temperature. The plates are then washed and color is developed using TMB Microwell peroxidase (KPL). Color development is stopped after 5 min with 50 μL 1N $H_2SO_4$. Absorbance is determined at 490 nm in a SpectraMax microplate spectrophotometer (Molecular Devices).

Neutralization Assays

Neutralization assays are performed as described above. Here, however, the objective is to test the ability of rabbit antisera compared to pre-immunization sera to reduce the infectivity of various HIV-1 isolates.

Example 6

Recognition of Native HIV-1 Env Epitopes by Antisera Induced by a Webbed Immunogen A desirable property in an HIV vaccine is the ability to induce antibodies that preferentially recognize native epitopes on the virus. Therefore, the extent of binding to native versus denatured gp120 is tested in capture ELISAs. Microtiter plates are coated with 5 μg/mL affinity purified sheep anti-HIV-1 gp120 (Cliniqa) and incubated overnight at 4° C. Plates are washed four times with the TBS-Tween solution described above. Plates are blocked with blotto, incubated 1 h at room temperature, and then washed with TBS-Tween. Antigen capture is achieved by applying 1 μg/mL native or denatured gp120 in 5% blotto and incubating at room temperature for 2 h. Gp120 is denatured by boiling for 5 min in 1% SDS (Fisher Scientific, Fair Lawn, N.J.) and 0.1 mM Dithiothreitol (DTT) (BioRad). Plates are washed four times as above, then, beginning at a 1:30 dilution, threefold serial dilutions of sera (in 2% blotto) are added in duplicate to the wells and incubated for 2 hr at room temperature. Plates are again washed four times with TBS-Tween, and alkaline phosphatase-conjugated anti-rabbit IgG diluted 1:2000 in a mixture of 2% blotto and 5% lamb serum is added and incubated at room temperature for 1 h. Plates are washed four times with TBS-Tween and color is developed using the ELISA amplification system (Invitrogen, Carlsbad, Calif.). Absorbance is determined at 490 nm using a SpectraMax microplate spectrophotometer (Molecular Devices, Sunnyvale, Calif.).

We claim:

1. A webbed human immunodeficiency virus type 1 (HIV-1) envelope immunogen comprising an admixture of the following:
   a) a recombinant HIV-1 envelope glycoprotein or truncated variant thereof; and
   b) a recombinant scorpion toxin M9 domain multimer;
      wherein said M9 multimer comprises the M9 protein fused to a peptide and that promotes the multimerization of M9;
   and wherein said HIV-1 envelope and M9 fusion protein upon admixing form a high-molecular weight, highly immunogenic aggregate through noncovalent associations.

2. The webbed HIV-1 envelope immunogen of claim 1, wherein said peptide that promotes the multimerization of M9 is the bacteriophage T4 fibritin protein.

3. The webbed HIV-1 envelope immunogen of claim 1, wherein said HIV-1 envelope glycoprotein is selected from the group consisting of rpg160, rpg140, rpg120, rgp160$_3$ and rgp140$_3$.

4. The webbed HIV-1 envelope immunogen of claim 1, wherein said HIV-1 envelope glycoprotein or truncated variant thereof is a recombinant HIV-1 envelope protein selected from the group consisting of subtype A, subtype B, subtype C, subtype D, subtype E, subtype J and dade G.

5. The webbed HIV-1 envelope immunogen of claim 1, wherein said HIV-1 envelope glycoprotein or truncated variant thereof is a truncated variant selected from the group consisting of rgp160, rgp140, rgp120, rgp160$_3$ and rgp140$_3$.

6. The webbed HIV-1 envelope immunogen of claim 1, wherein an HIV-envelope disulfide loop is replaced with amino acids 552-593 of the Ebola virus gp2 heptad repeat domain.

7. The webbed HIV-1 envelope immunogen of claim 1, wherein said recombinant HIV-1 envelope glycoprotein or truncated variant thereof comprises a rigid linker between gp120 and gp41.

8. The webbed HIV-1 envelope immunogen of claim 1, wherein said peptide that promotes the multimerization of M9 is selected from the group of bacteriophage T4 fibritin, Fc domain of non-human primate or human IgG or IgA, cholera toxin, or GCN4.

9. The webbed HIV-1 envelope immunogen of claim 1, wherein said scorpion toxin comprises a reporter tag.

10. The webbed HIV-1 envelope immunogen of claim 9, wherein said reporter tag comprises a poly (His) sequence.

11. The webbed HIV-1 envelope immunogen of claim 1, wherein either or both said recombinant HIV-1 envelope glycoprotein or truncated variant thereof, and said recombinant scorpion toxin M9 domain multimer comprise a leader sequence.

12. The webbed HIV-1 envelope immunogen of claim 11, wherein said leader sequence is from a source selected from the group consisting of human tissue plasminogen activator signal peptide, human interferon, human chromogranin, humans casein beta, tumor rejection antigen-1 gp96, and human zona pellucida glycoprotein 2 preprotein.

13. The webbed HIV-1 envelope immunogen of claim 1 wherein said recombinant HTV-1 envelope glycoprotein or truncated variant thereof and said multimer of a recombinant scorpion toxin M9 domain are associated by hydrogen bonding.

14. The webbed HIV-1 envelope immunogen of claim 1 wherein said HIV-1 envelope glycoprotein or truncated derivative thereof and said recombinant scorpion toxin M9 domain multimer are associated by Van der Waals forces.

* * * * *

SEQUENCE LISTING

```
<160> NUMBER OF SEQ ID NOS: 14

<210> SEQ ID NO 1
<211> LENGTH: 105
<212> TYPE: DNA
<213> ORGANISM: Homo sapiens

<400> SEQUENCE: 1
atggatgcaa tgaagagagg gctctgctgt gtgctgctgc tgtgtggagc agtcttcgtt      60
tcgcccagcc aggaaatcca tgcccgattc agaagaggag ccaga                    105

<210> SEQ ID NO 2
<211> LENGTH: 1443
<212> TYPE: DNA
<213> ORGANISM: Human immunodeficiency virus type 1

<400> SEQUENCE: 2
agcgccagcg agaacctgtg ggtgaccgtg tactacggcg tgcccgtgtg ggaggaggcc      60 gacaccccc tgttctgcgc cagcgacgcc aaggcctaca gcaccgagaa gcacaacgtg     120
tgggccaccc acgcctgcgt gcccaccgac cccaacccc aggagatcct gctgaagaac     180
gtgaccgagc ccttcaacat gtggaagaac aacatggtgg agcagatgca cgaggacatc     240
atcagcctgt gggacgagag cctgaagccc tgcgtgaagc tgacccccct gtgcgtgacc     300
ctggactgca tcaacgccaa cgtgtgcggc ggcaacagca ccggcaacag caccgaggcc     360
```

-continued

```
aacaccaccg cctgcagcag cgaggaggtg aagaactgca ccttcaacat caccaccgag    420
atccgcgacc gcgagaagaa ggagtacgcc ctgttctaca agctggacgt ggtgcagatc    480
gacaagaaca acaccaaccg ctaccgcctg ctgaactgca acgtgagcac catcaagcag    540
gcctgcccca aggtgacctt cgaccccatc cccatccact actgcgcacc tgccggcttc    600
gccatcctga agtgcaacga aagaacttc accggcatcg gcaagtgcaa gaacgtgagc    660
accgtgcagt gcacccacgg catcaagccc gtggtgagca cccagctgct gctgaacggc    720
agcctggccg aggaggagat cgtgatccgc agcgagaaca tcaccaacaa cgccaagatc    780
gtgatcgtgc agctgaacaa gagcatcgag atcaactgca ccaggcccag caacaacacc    840
cgccgcagca tcagcttcgg ccctggccag gccttctaca gcaccggcga ggtgatcggc    900
gacatccgca aggcccactg caacgtgaac agcaagaact ggaccgagat gctgaccgc     960 gtgaagatcc agctgaagaa gttcttcagc aacaccacca acatcacctt caaccagagc   1020
gccggtggcg acctggagat caccacccac agcttcaact gtaggggcga gttcttctac   1080
tgcgacacca gcaacctgtt caacatcagc gacagcaaca acagcaccag cgacagcaac   1140
gacaccatca ccatcccctg caagatcaag cagatcgtgc gcatgtggca gcgcgtgggc   1200
caggccatgt acgcccctcc catcgctggc aacatcatct gcgtgagcaa catcaccggc   1260
ctgctgctga cccgcgacgg cggccacaac gtgaccaacg agaccgagat cttccgccct   1320
ggcggaggcg acatgcgcga caactggcgc agcgagctgt acaagtacaa gatcgtgaag   1380
atcaagcccc tgggcatcgc ccctaccccgc gcacgccgca gggtggtgga gcgcgagaag   1440
acc                                                                1443

<210> SEQ ID NO 3
<211> LENGTH: 12
<212> TYPE: DNA
<213> ORGANISM: Artificial
<220> FEATURE:
<223> OTHER INFORMATION: rigid linker sequence

<400> SEQUENCE: 3
ccctcctccc cc                                                         12

<210> SEQ ID NO 4
<211> LENGTH: 108
<212> TYPE: DNA
<213> ORGANISM: Human immunodeficiency virus type 1

<400> SEQUENCE: 4
tccggcatcg tgcagcagca gtccaacctg ctgcgcgcca tcgaggccca gcagcacctg    60
ctgaagctga ccgtgtgggg catcaagcag ctgcaggccc gcgtgctg                108

<210> SEQ ID NO 5
<211> LENGTH: 126
<212> TYPE: DNA
<213> ORGANISM: Ebola virus

<400> SEQUENCE: 5
gacggcctga tctgcggcct cgccagctg gccaacgaga ccacccaggc cctgcagctg    60
ttcctgcgcg ccaccaccga gctgcgcacc ttctccatcc tgaaccgcaa ggccatcgac   120
ttcctg                                                              126

<210> SEQ ID NO 6
<211> LENGTH: 102
```

-continued

<212> TYPE: DNA
<213> ORGANISM: Human immunodeficiency virus type 1

<400> SEQUENCE: 6
tggcgcgact gggacaagga gatctccaag tacacccgca tcatctacga cctgatcgag 60
gagtcccaga accagcagga gaagaacgag caggacctgc tg 102

<210> SEQ ID NO 7
<211> LENGTH: 69
<212> TYPE: DNA
<213> ORGANISM: Human immunodeficiency virus type 1

<400> SEQUENCE: 7
gccctggaca agtgggcctc cctgtggaac tggttcgaca tctccaactg gctgtggtac 60
atcaagatc 69

<210> SEQ ID NO 8
<211> LENGTH: 63
<212> TYPE: DNA
<213> ORGANISM: Human immunodeficiency virus type 1

<400> SEQUENCE: 8
ttcatcatga tcgtgggcgg cctgatcggc ctgcgcatcg tgttcgccgt gctgtccatc 60
gtg 63

<210> SEQ ID NO 9
<211> LENGTH: 21
<212> TYPE: DNA
<213> ORGANISM: Artificial
<220> FEATURE:
<223> OTHER INFORMATION: coding for a polyhistidine tag

<400> SEQUENCE: 9
catcatcacc atcaccattg a 21

<210> SEQ ID NO 10
<211> LENGTH: 105
<212> TYPE: DNA
<213> ORGANISM: Homo sapiens

<400> SEQUENCE: 10
atggatgcaa tgaagagagg gctctgctgt gtgctgctgc tgtgtggagc agtcttcgtt 60
tcgcccagcc aggaaatcca tgcccgattc agaagaggag ccaga 105

<210> SEQ ID NO 11
<211> LENGTH: 84
<212> TYPE: DNA
<213> ORGANISM: Buthus eupeus

<400> SEQUENCE: 11
tgcaacctgg cccgctgcca gctgcgctgc aagtccctgg gcctgctggg caagtgcgcc 60
ggctccttct gcgcctgcgt gaag 84

<210> SEQ ID NO 12
<211> LENGTH: 33
<212> TYPE: DNA
<213> ORGANISM: Artificial
<220> FEATURE:
<223> OTHER INFORMATION: linker sequence

<400> SEQUENCE: 12

```
ggctcctccc cctcccctc ctccctcc ccc                                              33

<210> SEQ ID NO 13
<211> LENGTH: 81
<212> TYPE: DNA
<213> ORGANISM: Bacteriophage T4

<400> SEQUENCE: 13
ggctacatcc ccgaggcccc ccgcgacggc caggcctacg tgcgcaagga cggcgagtgg             60
gtgctgctgt ccaccttcct g                                                        81

<210> SEQ ID NO 14
<211> LENGTH: 21
<212> TYPE: DNA
<213> ORGANISM: Artificial
<220> FEATURE:
<223> OTHER INFORMATION: codign for a polyhistidine tag

<400> SEQUENCE: 14
catcatcacc atcaccattg a                                                        21
```